US012636406B2

(12) United States Patent
Rosines

(10) Patent No.: US 12,636,406 B2
(45) Date of Patent: *May 26, 2026

(54) BIOLOGICAL PROSTHESIS AND METHODS OF PRODUCTION AND USE

(71) Applicant: Rosivo LLC, Salt Lake City, UT (US)

(72) Inventor: Eran Rosines, Salt Lake City, UT (US)

(73) Assignee: Rosivo LLC, Salt Lake City, UT (US)

( * ) Notice: Subject to any disclaimer, the term of this patent is extended or adjusted under 35 U.S.C. 154(b) by 186 days.

This patent is subject to a terminal disclaimer.

(21) Appl. No.: 18/472,708

(22) Filed: Sep. 22, 2023

(65) Prior Publication Data

US 2024/0016980 A1     Jan. 18, 2024

Related U.S. Application Data

(60) Continuation of application No. 17/069,397, filed on Oct. 13, 2020, now Pat. No. 11,801,330, which is a continuation of application No. 15/994,740, filed on May 31, 2018, now Pat. No. 10,814,035, which is a division of application No. 14/477,797, filed on Sep. 4, 2014, now Pat. No. 10,016,528.

(60) Provisional application No. 61/875,122, filed on Sep. 9, 2013.

(51) Int. Cl.
*A61L 27/36*          (2006.01)

(52) U.S. Cl.
CPC ....... *A61L 27/3612* (2013.01); *A61L 27/3687* (2013.01); *A61L 27/3695* (2013.01); *A61L 2430/06* (2013.01)

(58) Field of Classification Search
CPC ............. A61L 27/3687; A61L 27/3695; A61L 2430/06; A61L 27/3604; A61L 27/3612; A61L 27/362
See application file for complete search history.

(56) References Cited

U.S. PATENT DOCUMENTS

| | | | |
|---|---|---|---|
| 3,314,861 A | 4/1967 | Tadahiko | |
| 5,035,715 A | 7/1991 | Smestad et al. | |
| 5,128,326 A | 7/1992 | Balazs et al. | |
| 5,782,915 A | 7/1998 | Stone | |
| 5,989,498 A | 11/1999 | Odland | |
| 6,117,979 A | 9/2000 | Hendriks et al. | |
| 6,166,184 A | 12/2000 | Hendriks et al. | |
| 6,203,755 B1 | 3/2001 | Odland | |
| 6,734,018 B2 | 5/2004 | Wolfinbarger, Jr. et al. | |
| 7,053,051 B2 | 5/2006 | Hendrikcs et al. | |
| 8,697,442 B2 | 4/2014 | Hendriks et al. | |
| 8,901,078 B2 | 12/2014 | Mezger et al. | |
| 9,072,819 B2 | 7/2015 | Hendriks et al. | |
| 9,220,808 B2 | 12/2015 | Mezger et al. | |
| 9,399,084 B2 | 7/2016 | Mezger et al. | |
| 9,592,320 B2 | 3/2017 | Mezger et al. | |
| 10,016,528 B2 * | 7/2018 | Rosines ............. | A61L 27/3687 |
| 10,561,762 B2 | 2/2020 | Rosines | |
| 10,611,822 B2 | 4/2020 | Mezger et al. | |
| 10,814,035 B2 * | 10/2020 | Rosines .............. | A61L 27/3612 |
| 11,801,330 B2 * | 10/2023 | Rosines .............. | A61L 27/3687 |
| 2008/0077251 A1 | 3/2008 | Chen et al. | |
| 2009/0012627 A1 | 1/2009 | Claesson et al. | |
| 2010/0174374 A1 | 7/2010 | Haines | |
| 2011/0195107 A1 | 8/2011 | Min et al. | |
| 2012/0282226 A1 | 11/2012 | Ayares et al. | |
| 2013/0030526 A1 | 1/2013 | Mezger et al. | |
| 2016/0000970 A1 | 1/2016 | Rosines | |

FOREIGN PATENT DOCUMENTS

| | | | |
|---|---|---|---|
| EP | 0640647 A2 | 3/1995 | |
| WO | 1996025961 A1 | 8/1996 | |
| WO | 1997017430 A1 | 5/1997 | |
| WO | 2006026325 A2 | 3/2006 | |
| WO | 2010108945 A1 | 9/2010 | |
| WO | 2013036568 A1 | 3/2013 | |

OTHER PUBLICATIONS

Alexander Florian Elsaesser et al., In Vitro Cytotoxicity and In Vivo Effects of a Decellularized Xenogeneic Collagen Scaffold in Nasal Cartilage Repair, Tissue Engineering: Part A, vol. 20, No. 11 and 12, 2014, pp. 1668-1678.
Raymond Zeeman et al., The Kinetics of 1,4-Butanediol Diglycidyl Ether Cross/inking of Dermal Sheep Collagen, J. Biomed Mater Res., vol. 15, No. 51 (4), Sep. 2000, pp. 541-548.
Damink et al. "Glutaraldehyde as a crosslinking agent for collagen-based biomaterials," Journal of Materials Science: Materials in Medicine. Aug. 1995, vol. 6, pp. 460-472 entire document.
Kaukinen et al. "Destructive Testing of Articular Cartilage in Compression-Effect of Collagen Network," 2005, 51 st Annual Meeting of the Orthopaedic Research Society, Poster No. 1691, available at http://www.ors.or_g/transactions/51/1691.pdf entire document.
Hovakimyan et al. "Collagen cross-linking: current status and future directions," J Ophthalmol. Jan. 12, 2012 (Jan. 12, 2012), Article ID 406850, pp. 1-12. entire document.
Wong et al. "Stepwise solubilization-based antingen removal for xenogeneic scaffold generation in tissue engineering," Acta Biomater. Jan. 12, 2013 (Jan. 12, 2013), vol. 9, pp. 6492-6501. entire document.

(Continued)

*Primary Examiner* — Aaron J Kosar
(74) *Attorney, Agent, or Firm* — Workman Nydegger

(57) ABSTRACT

Products, processes, compositions, kits, and methods are provided for cartilage-derived implants. The implants can exhibit resistance to enzyme (e.g., collagenase, protease, etc.) digestion compared to the source tissue from which they were derived while still having one or more mechanical properties comparable to the source tissue from which they were derived. The implants can also have a plurality of molecular bridges between molecules of the cartilaginous material. The molecular bridges can connect one or more collagen fibrils and/or with one or more glycosaminoglycans. The implants can also be treated with cationic detergent, packaged and sterilized with or without additional components, and surgically implanted into subjects.

27 Claims, 10 Drawing Sheets

(56) References Cited

OTHER PUBLICATIONS

Aparecida Da Silva Aquino, K. "Chapter 9: Sterilization by Gamma Irradiation," Mar. 21, 2012 (Mar. 21, 2012). Gamma Radiation, Edited by Adrovic, pp. 171-206, available at http://cdn.intechopen.com/pdfs-wm/32842.pdf entire document.

Ali, Sy "The Degradation of Cartilage Matrix by an Intracellular Protease" Biochem. J. (1964), 93, 611-618.

Cavallito CJ "Quaternary ammonium salts—advances in chemistry and pharmacology since 1960" Progress in Drug Research, (B. Berde et al.(ed.)), pp. 267-373.

Feng Yu et al. "An interpenetrating HAIG/CS biomimic hydrogel via Diels-Alder click chemistry for cartilage tissue engineering", Carbohydrate Polymers, Apr. 26, 2013, pp. 188-195, vol. 97, No. 1, Applied Science Publishers, LTD., Barking GB.

Henrique V. Almeida et al. "Controlled release of transforming growth factor-133 from cartilage-extra-cellular-matrix-derived scaffolds to promote chondrogenesis of human-joint-tissue-derived stem cells", Acta Biomaterialia, Jun. 4, 2014, pp. 4400-4409, vol. 10, No. 10.

Decision to Grant received for European Patent Application No. 14841988, mailed on Oct. 10, 2019, 2 pages.

European Search Report received for EP Patent Application No. 14841988, mailed on Apr. 28, 2017, 8 pages.

Feng Yu et al. "An interpenetrating HA/G/CS biomimic hydrogel via Diels-Alder click chemistry for cartilage tissue engineering", Carbohydrate Polymers, Apr. 26, 2013, pp. 188-195, vol. 97, No. 1, Applied Science Publishers, LTD., Barking GB.

Henrique V. Almeida et al. "Controlled release of transforming growth factor-ß3 from cartilage-extra-cellular-matrix-derived scaffolds to promote chondrogenesis of human-joint-tissue-derived stem cells", Acta Biomaterialia, Jun. 4, 2014, pp. 4400-4409, vol. 10, No. 10.

Hermansson, M. et al, "Proteomic Analysis of Articular Cartilage Shows Increased Type II Collagen Synthesis in Osteoarthritis and Expression of Inhibin .Beta.-A (Activin A), a Regulatory Molecule for Chondrocytes", JBC, 279(2), Oct. 15, 2004 (ePub Aug. 2, 2004), pp. 43514-43521; DOI 10.1074/jbc.M407041200. (Year: 2004).

Intention to grant received for European Patent Application No. 14841988, mailed on Apr. 23, 2019, 6 pages.

International Preliminary Report on Patentability received for PCT Patent Application No. PCT/US2014/054386, mailed on Mar. 24, 2016, 16 pages.

International Search Report and Written Opinion received for PCT Patent Application No. PCT/US2014/054386, mailed on Dec. 31, 2014, 19 pages.

Notice of Allowance received for U.S. Appl. No. 14/477,797, mailed on Jan. 18, 2018.

Office Action received for European Patent Application No. 14841988, mailed on Apr. 25, 2018, 6 pages.

Office Action received for U.S. Appl. No. 14/477,797, mailed on Jan. 3, 2017.

Office Action received for U.S. Appl. No. 14/477,797, mailed on Jul. 5, 2016.

Office Action received for U.S. Appl. No. 14/477,797, mailed on Sep. 22, 2017.

U.S. Appl. No. 61/875,122, filed Sep. 9, 2013, Rosines.

* cited by examiner

Residual Galactose-alpha-1,3-galactose

BIOLOGICAL PROSTHESIS AND METHODS OF PRODUCTION AND USE

CROSS-REFERENCE TO RELATED APPLICATIONS

This application is a continuation of U.S. application Ser. No. 17/069,397, filed Oct. 13, 2020, which is a continuation of U.S. application Ser. No. 15/994,740, filed May 31, 2018, now U.S. Pat. No. 10,814,035, which is a Divisional of U.S. application Ser. No. 14/477,797, filed Sep. 4, 2014, now U.S. Pat. No. 10,016,528, which claims the benefit of and priority to U.S. Provisional Application Ser. No. 61/875,122, filed Sep. 9, 2013, the entirety of each of which is incorporated herein by reference.

BACKGROUND OF THE INVENTION

1. The Field of the Invention

The present invention relates to biological implant materials for repair and reconstruction of cartilage-based tissues. More specifically, the present invention relates to cartilage-derived implants, methods of producing cartilage-derived implants, and methods of use for cartilage-derived implants for repair and reconstruction of the nose, ear, trachea, articular surfaces and other cartilage-based tissues.

2. The Relevant Technology

Plastic surgery of the nose, or rhinoplasty, often requires the use of cartilaginous implants to reconstruct and repair the underlying structures that comprise the nose. For many surgeons, the preferred implant material is a patient's own septal, auricular, or costal cartilage (collectively referred to as autologous cartilage). However, there is a limited amount of available autologous cartilage for use in repair, and often there is not enough availability for a given procedure (particularly revision procedures). Accordingly, autologous cartilage often cannot provide a large enough segment of cartilage for a given type of repair procedure. The harvesting of cartilage is also a time consuming procedure that results in donor site morbidity. Elderly or other medically compromised patients often cannot withstand the extra anesthesia time or invasiveness associated with the harvesting procedure. Furthermore, although autologous cartilage does not cause a foreign body response, over time autologous cartilage can be resorbed by the body.

One alternative to autologous cartilage is a synthetic implant. Two examples of structural synthetic implant materials include porous high density polyethylene (pHDPE) and silicone. However, synthetic implants used in nasal reconstruction possess known deficiencies including high rates of extrusion, unnatural feel, significantly higher infection rates, the need for removal when infected, high rates of migration, and ultimately, failure rates higher than autologous cartilage grafting. Despite the critical need for implants, surgeons often avoid the use of synthetic implants.

Allogenic or donated human tissue is another option for nasal reconstruction. Cartilage from the rib (costal cartilage), can be recovered from a donor and then processed into a final implant material. Typically, the cartilage is rinsed with various solutions and then gamma irradiated. The disadvantages of this implant material likewise include the limited availability of donor human tissue supply. Furthermore, costal cartilage does not have the same mechanical feel and flexibility as nasal cartilage, human cell remnants in the cartilage retain the potential to be recognized as a foreign body, and costal cartilage implants exhibit high rates of warping, making allogenic or donated human tissue an impractical and undesirable alternative.

Materials for use in some medical therapies may also be derived from animal tissue sources. The animal-derived source material is typically processed in a way that is intended to make the material compatible with the human body. These processing methods may include steps to remove cellular and antigenic substances from the source materials, crosslinking, and sterilization. However, known processing methods often include the use of harsh alcohols and detergent that irreversibly dry and damage cartilage by harming the molecular components, alter the biochemical or biomechanical properties of the cartilage, require excessive processing times, and employ additional expensive antibiotic components. Likewise, known methods of crosslinking (to protect the tissue from degradation when implanted into a human) may result in a change in mechanical properties and results in a change in how the body reacts to the tissue. These reactions can include calcification, excessive fibrous tissue deposition, and rejection. Cartilage, in particular, has biochemical and biomechanical properties that make the tissue particularly sensitive to current processing techniques.

Accordingly, there are a number of disadvantages in conventional cartilage-derived implants that can be addressed.

SUMMARY OF THE INVENTION

The present invention relates to cartilage-derived tissue that has been processed to be biocompatible for human implantation. For instance, an embodiment includes a cartilage-derived implant that is essentially void of living cells (from the source organism), resistant to cellular infiltration, optionally resistant to enzymatic resorption, and/or mechanically comparable in feel and/or strength compared to the source cartilage material. In at least one embodiment, the source cartilage can be derived from the septal, auricular, and/or articular cartilage of a pig, horse, cow, canine, human, or other animal.

The present invention also relates to methods of processing animal-derived cartilage into a cartilage-derived implant possessing one or more of the characteristics described herein. In some embodiments, the method comprises treating the cartilage with a cationic detergent solution. In some embodiments, the method comprises treating the cartilage with a stabilizing agent that forms molecular bridges within the cartilage-derived implant. Some embodiments include a (terminal) sterilization step (e.g., gamma and/or electron beam irradiation).

The present invention also relates to methods of use for a cartilage-derived implant. In some embodiments, the cartilage-derived implant is used for repairing or reconstructing cartilaginous structures. In some embodiments the method comprises obtaining the cartilage-derived implant described herein, sculpting the cartilage-derived implant into a specific shape, and/or implanting the cartilage-derived implant into an anatomical location (e.g., a nose or ear requiring repair with a cartilage-derived implant).

Additional features and advantages of exemplary embodiments of the present disclosure will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

DETAILED DESCRIPTION OF THE INVENTION

Figure 1A:
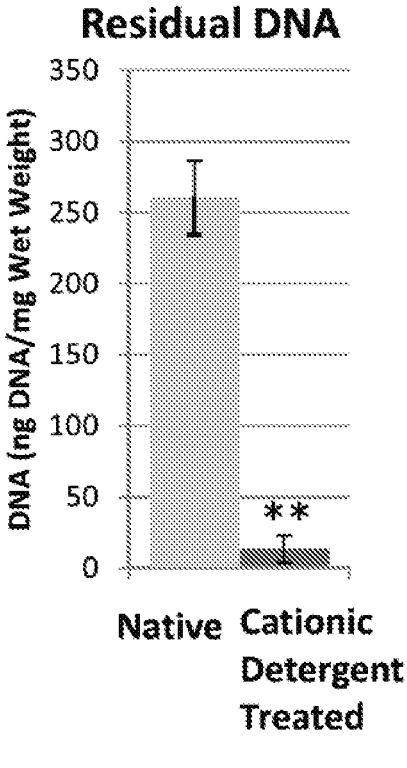
FIG. 1A illustrates an exemplary reduction in residual DNA following cationic detergent treatment according to an embodiment of the present invention.

Before describing the present disclosure in detail, it is to be understood that this disclosure is not limited to parameters of the particularly exemplified products, processes, compositions, kits, and/or methods, which may, of course, vary. It is also to be understood that the terminology used herein is only for the purpose of describing particular embodiments of the present invention, and is not intended to limit the scope of the invention in any manner.

All publications, patents, and patent applications cited herein, whether supra or infra, are hereby incorporated by reference in their entirety to the same extent as if each individual publication, patent, or patent application was specifically and individually indicated to be incorporated by reference.

Additionally, the terms "including," "having," "involving," "containing," "characterized by," and variants thereof (e.g., "includes," "has," and "involves," "contains," etc.) as used herein, including the claims, shall be inclusive and/or open ended, shall have the same meaning as the word "comprising" and variants thereof (e.g., "comprise" and "comprises"), and does not exclude additional, unrecited elements or method steps, illustratively.

It will be noted that, as used in this specification and the appended claims, the singular forms "a," "an" and "the" include plural referents unless the content clearly dictates otherwise. Thus, for example, reference to a "support member" includes one, two, or more support members.

Various aspects of the present invention may be illustrated with reference to one or more exemplary embodiments. As used herein, the term "exemplary" means "serving as an example, instance, or illustration," and should not necessarily be construed as preferred or advantageous over other embodiments disclosed herein.

It will also be appreciated that where a range of values (e.g., less than, greater than, at least, or up to a certain value, or between two recited values) is disclosed or recited, any specific value or range of values falling within the disclosed range of values is likewise disclosed and contemplated herein. Thus, disclosure of a pH between 5 and 9 includes, illustratively a specific disclosure of: (i) a pH of 5.2, 6.5, 8, or any other value between 5 and 9; and/or (ii) a pH between and 8, a pH between 6 and 9, a pH between 7 and 8, and/or any other smaller range of values between 5 and 9.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only preferred materials and methods are described herein.

The present invention relates to a cartilage-derived implant that has been processed to be biocompatible for or upon human implantation. For instance, the cartilage-derived implant can be sterile within a defined sterility assurance level. The cartilage-derived implant can also have or exhibit a reduced level (or be essentially void or free) of residual source organism (living) cells and/or cellular remnants compared to the source cartilage. Accordingly, the chance of a non-allergic foreign body rejection of the cartilage-derived implant upon implantation (e.g., into a human) can be reduced or eliminated.

The cartilage-derived implant can also be resistant to or against cellular infiltration and/or enzymatic digestion (e.g., degradation and/or resorption). The cartilage-derived implant can also be biomechanically and/or biochemically comparable to the source cartilage material. For instance, the cartilage-derived implant can have or exhibit increased stability compared to the source cartilage while retaining mechanical properties substantially similar to the source cartilage such that the cartilage-derived implant is comparable in feel and/or mechanical property to natural cartilage when it is implanted in a body. Accordingly, one will appreciate that reference to "processed cartilage" and similar terms can refer to a cartilage-derived implant that has been processed to effectuate any one or more of the above-identified or other characteristic or properties. In at least one embodiment, the source cartilage can be derived from the septal, auricular, costal, and/or articular cartilage of a pig, horse, cow, canine, human, or other animal.

One will appreciate that reference to an implant is exemplary, and various configurations, designs, intended uses, etc. are known in the art and contemplated herein. For purposes of illustration only, this disclosure refers to implants designed for human implantation. One will appreciate, however, that non-human implantation and non-implantation uses for the cartilage-derived tissue disclosed herein are also within the scope of this disclosure.

As will be discussed in further detail below, processing cartilage (e.g., to effectuate any one or more of the above-identified or other characteristic or properties) can be achieved by treatment with a cationic detergent (e.g., to remove source cells and/or cellular remnants). Accordingly, in one or more embodiments, the cartilage-derived implant (or composition thereof) can comprise or be associated with at least a residual or trace amount of a cationic detergent. In at least one embodiment, cationic detergent treatment can remove an amount of living cells and/or cellular remnants from the source cartilage.

In some embodiments, the processed, cartilage-derived implant may include an amount of: (i) living cells; (ii) living cells of the donor or source organism; and/or (iii) cellular remnants, the amount being sufficiently small such that the chance of a non-allergic foreign body rejection upon implantation (e.g., into a human) is reduced compared to the source cartilage. In some embodiments, the cartilage-derived implant may include an amount of: (i) living cells; (ii) living cells of the donor or source organism; and/or (iii) cellular remnants, the amount being within (agency) standards (e.g., FDA) for the cartilage-derived implant (e.g., to be used as a medical device or implant).

For instance, in some embodiments, the cartilage-derived implant is essentially void of living cells (e.g., of the donor or source organism) and/or cellular remnants. As used herein, "essentially void" and similar terms can refer to undetectable amounts (by one or more, or all, current detection methods). In addition, "essentially void" and similar terms can refer to less than 0.01%, less than 0.1%, less than 1%, less than 2%, less than 3%, less than 4%, less than 5%, less than 6%, less than 7%, less than 8%, less than 9%, less than 10%, less than 12%, less than 15%, less than 20%, less than 25%, less than 30%, or less than 35% compared to an original amount or control amount of the component present in the source cartilage or explant.

In some embodiments, the cartilage-derived implant comprises a reduced amount of living cells and/or cellular remnants (e.g., compared to the source cartilage). As used herein, "reduced amount" and similar terms can refer to any statistically significant decrease in an amount compared to a standard (e.g., the source cartilage from which a cartilage-derived implant was derived). For instance, in some embodiments, the cartilage-derived implant can comprise or retain less than 0.0001%, less than 0.001%, less than 0.01%, less than 0.1%, less than 1%, less than 2%, less than 3%, less than 4%, less than 5%, less than 6%, less than 7%, less than 8%, less than 9%, less than 10%, less than 15%, less than 20%, less than 25%, less than 30%, or less than 35% of living cells and/or living cells of the donor or source organism. Similarly, in certain embodiments, the cartilage-derived implant has been processed in order to remove at least some of the living cells and/or cellular remnants of or from the source cartilage.

As used herein, "cellular remnants" and similar terms can refer to DNA, RNA, soluble proteins, immunogenic proteins, immunogenic effectors, major histocompatibility complex (MHC) proteins, galactose-alpha-1,3-galactose, blood, and/or cellular vestiges or debris of the donor or source organism (e.g., not including structural components of cartilage and/or the extra-cellular matrix (ECM) of the donor or source organism). In at least one embodiment, a cartilage-derived implant can exhibit up to, at least, greater than, or approximately a 400-fold decrease in the level or amount of residual, source organism DNA (w/w) compared to the source cartilage. For instance, as illustrated in FIG. 1A, native, source cartilage can comprise approximately 260 ng DNA per mg wet weight cartilage. Processed cartilage (i.e., a cartilage-derived implant), on the other hand, can comprise approximately 13 ng DNA per mg wet weight cartilage. Thus, a cartilage-derived implant can exhibit up to, at least, greater than, or approximately a 95% reduction in the level or amount of source organism DNA (w/w) compared to the native, unprocessed, source tissue ($p=1.0^{-12}$).

One will appreciate, however, that other levels of DNA reduction (or amounts of residual DNA) are contemplated herein. For instance, a processed, cartilage-derived implant can exhibit up to, at least, greater than, or approximately a 2-fold, 3-fold, 4-fold, 5-fold, 10-fold, 20-fold, 50-fold, 100-fold, 250-fold, 500-fold, or 1000-fold decrease in the level or amount of residual, source organism DNA (compared to the source tissue). Likewise, processed tissue can exhibit greater than a 25%, 50%, 75%, 80%, 85%, 90%, 91%, 92%, 93%, 94%, 95%, 96%, 97%, 98%, or 99% decrease in the amount of source organism DNA (compared to the source tissue), or any value or range therebetween. One will also appreciate that different tissue samples and/or different organisms can exhibit varying amounts of DNA in their native, unprocessed state.

In at least one embodiment, the amount of residual DNA associated with a cartilage-derived implant can represent the amount of living cells and/or cellular remnant(s) associated with a cartilage-derived implant. For instance, in some embodiments, residual DNA levels can provide an indication of the amount of living cells and/or cellular remnants present in the cartilage-derived implant or other cartilaginous sample. In particular, the amount of residual DNA can represent the amount immunogenic proteins, immunogenic effectors, galactose-alpha-1,3-galactose, and/or major histocompatibility complex (MHC) proteins, which can trigger an immune response in the implant host or patient. Accordingly, in at least one embodiment, the cartilage-derived implant comprises a reduced amount of one or more immunogenic proteins, immunogenic effectors, galactose-alpha-1,3-galactose, and/or major histocompatibility complex (MHC) proteins, compared to the cartilage explant or unprocessed cartilage. For instance, in some embodiments, the cartilage-derived implant has been processed in order to remove some or essentially all galactose-alpha-1,3-galactose from the source cartilage explant. Furthermore, as discussed in further detail below, in some embodiments, cationic detergent treatment can have or provide the advantage of more effectively removing galactose-alpha-1,3-galactose and/or MHC proteins from the source cartilage compared to other non-cationic detergent washes.

In some embodiments, the source cartilage is derived from an animal genetically deficient in expression of galactose-alpha-1,3-galactose. Likewise, in some embodiments, the source cartilage is derived from an animal that expresses reduced levels of galactose-alpha-1,3-galactose. For instance, in some embodiments, the source cartilage is derived from an animal (e.g., a non-human animal) genetically altered to express no or reduced levels of galactose-alpha-1,3-galactose. In some embodiments, the source cartilage is derived from an animal genetically altered to express one or more human proteins. In some embodiments, the cartilage-derived implant comprises a reduced amount and/or is essentially void of both cellular remnants and galactose-alpha-1,3-galactose.

In at least one embodiment, cationic detergent treatment can remove an amount of living cells and/or cellular remnants from the source cartilage while not significantly altering one or more biochemical and/or biomechanical properties of the cartilage. Accordingly, in some embodiments, the cartilage-derived implant has or exhibits one or more comparable biomechanical properties relative to the source cartilage. For instance, the cartilage-derived implant can have or exhibit comparable biomechanical strength (e.g., as measured by compressive yield stress), compressibility, yield strain at break, elasticity, instantaneous stiffness, tensile strength, tensile strain, coefficient of friction, resilience, shock absorption, feel, Young's modulus, and/or other biomechanical properties relative to the source cartilage. Likewise, cationic detergent treatment can remove an amount of living cells and/or cellular remnants from the source cartilage while leaving the extra-cellular matrix structure of the cartilage substantially intact.

In some embodiments, "comparable" (e.g., biomechanical properties) "substantially the same," and similar terms can refer to and/or be defined as: a measurement value that falls within the range of the natural variation of that measurement value for the source cartilage; a measurement value within or less than 0.1%, 1%, 2%, 3%, 4%, 5%, 10%, 15%, 20%, or 25% of the average or range of the natural variation of that measurement value for the source cartilage; and/or a measurement value within a statistically relevant deviation or error value for the range of the natural variation of that measurement value for the source cartilage. For instance, a value that is comparable or substantially the same as one or more reference values can be within one standard deviation of the average of the reference values.

Figure 1B:
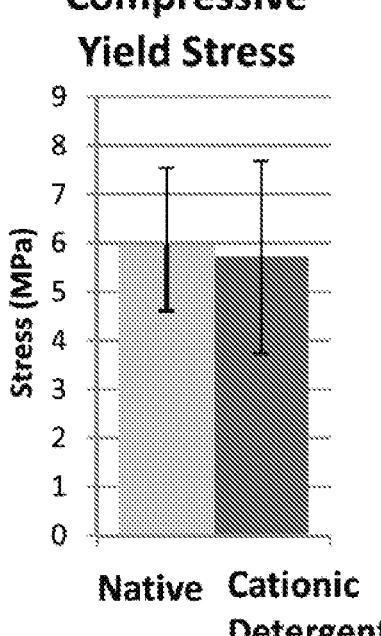
FIG. 1B illustrates an exemplary retention in compressive yield stress following cationic detergent treatment according to an embodiment of the present invention.

As illustrated in FIG. 1B, processed, cationic detergent-treated cartilage can retain a comparable level of biomechanical (compressive yield) strength (relative to the native, unprocessed, source cartilage). In the illustrated embodiment, native, unprocessed, source cartilage has a compressive yield stress value of approximately 5.9 MPa (Std. Dev.=1.6) and processed, cationic detergent-treated cartilage has a compressive yield stress value of approximately 5.7 MPa (Std. Dev.=2.0). Thus, the compressive yield stress value of the processed, cationic detergent-treated cartilage falls within the range of the natural variation of the compressive yield stress value for the source cartilage or within a statistically relevant deviation or error value for the range of the natural variation of the compressive yield stress value for the source cartilage. Thus, processed cartilage-derived implants can retain one or more biomechanical properties of the source cartilage (e.g., while having a reduced level of source cartilage explant-associated cells and/or cellular remnants).

In at least one embodiment, the cartilage-derived implant has or exhibits one or more comparable biochemical properties (e.g., relative to the source cartilage). For instance, the cartilage-derived implant can have or exhibit a molecular composition comparable to the source cartilage. In some embodiments, the cartilage-derived implant can retain one or more vital biochemical components of cartilage (e.g., glycosaminoglycans (GAGs) and/or (type II) collagen). One will appreciate that certain embodiments of the present invention can comprise a cartilage-derived implant having one or more biochemical components of cartilage in an altered or modified biochemical or molecular form (e.g., structure) without departing from the scope of this disclosure. For instance, as will be discussed in further detail below, embodiments of the present invention can comprise a cartilage-derived implant having crosslinked GAGs and/or collagen (fibrils).

Figure 2A:
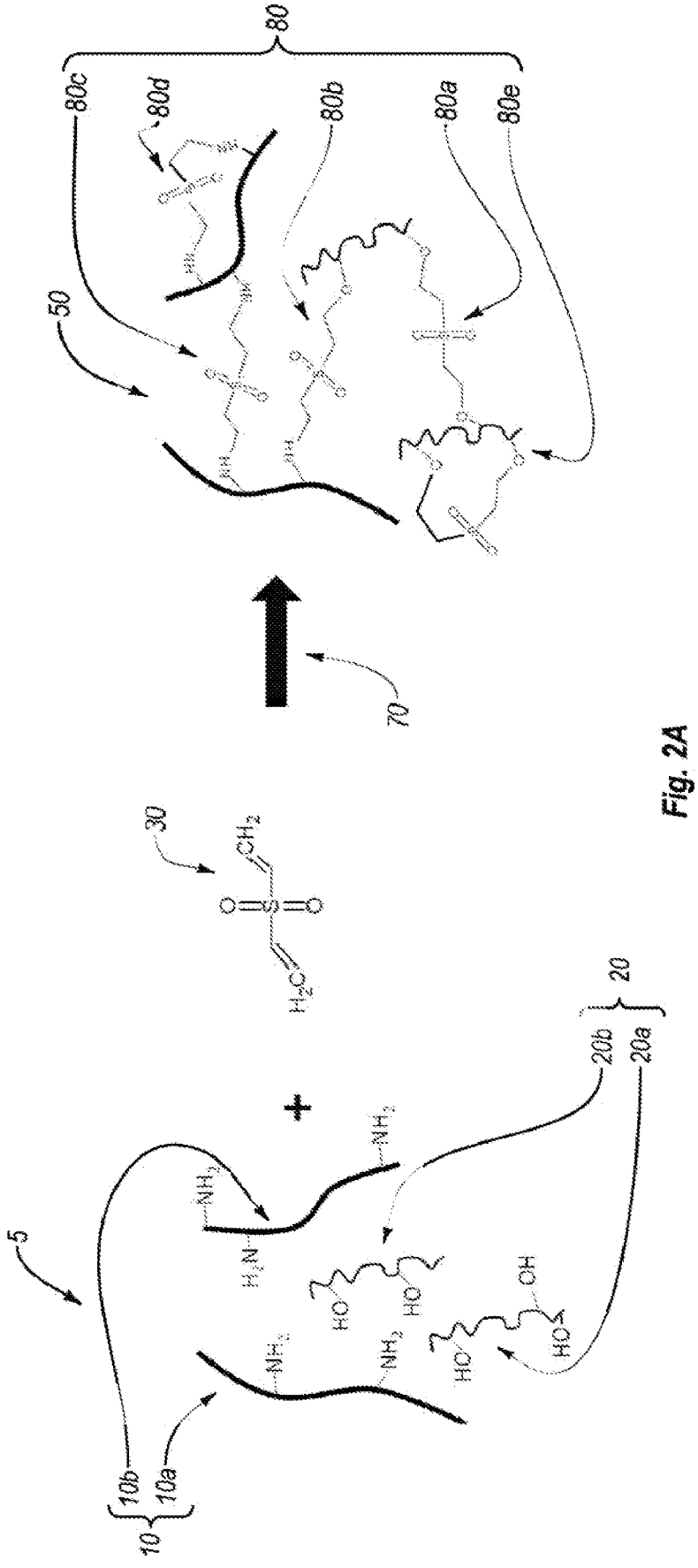
FIG. 2A illustrates an exemplary crosslinking reaction according to an embodiment of the present invention.

In some embodiments, the cartilage-derived implant comprises one or more molecular bridges or crosslinks between the macromolecules that comprise the source cartilage. In at least one embodiment, the macromolecules that comprise cartilage include GAGs and proteins, including collagen. Referring now to FIG. 2A, some embodiments comprise one or more sulfone-containing bridges that are covalently bonded to a GAG by an ether bond and/or covalently bonded to protein by a secondary amine bond. In certain embodiments, one or more sulfone-containing bridges can link: (i) a hydroxyl group of a first GAG to an adjacent hydroxyl group of the same or different GAG; (ii) a hydroxyl group of a GAG to an adjacent amine group of an adjacent protein (e.g., collagen); or (iii) an amine group of a protein to an adjacent amine group of the same or different protein.

For illustrative purposes only, FIG. 2A illustrates cartilage 5, comprising two collagen fibrils 10 and two GAG molecules 20. Collagen fibril 10a has two free amine groups and collagen fibril 10b has three free amine groups available to form bridges. Similarly, GAG 20a has three free hydroxyl groups and GAG 20b has two free hydroxyl groups available to form bridges. FIG. 2A also illustrates crosslinker 30. Crosslinker 30 can comprise a sulfone (e.g., divinyl sulfone or another reactive compound operable for generating one or more sulfone-containing bridges between molecules of cartilage 5).

Following reaction 70, crosslinked cartilage 50 comprises: (i) a sulfone-containing bridge 80a between a hydroxyl group of a first GAG and a hydroxyl group of a second GAG; (ii) a sulfone-containing bridge 80b between a hydroxyl group of a GAG and an amine group of a collagen fibril; (iii) a sulfone-containing bridge 80c between an amine group of a first collagen fibril and an amine group of a second collagen fibril; (iv); a sulfone-containing bridge 80d between amine groups of the second collagen fibril; and (v) a sulfone-containing bridge 80e between hydroxyl groups of the second GAG. One will appreciate that in certain embodiments, reaction conditions can promote the formation of one or more specific type(s) of sulfone-containing bridges 80.

Figure 2B:
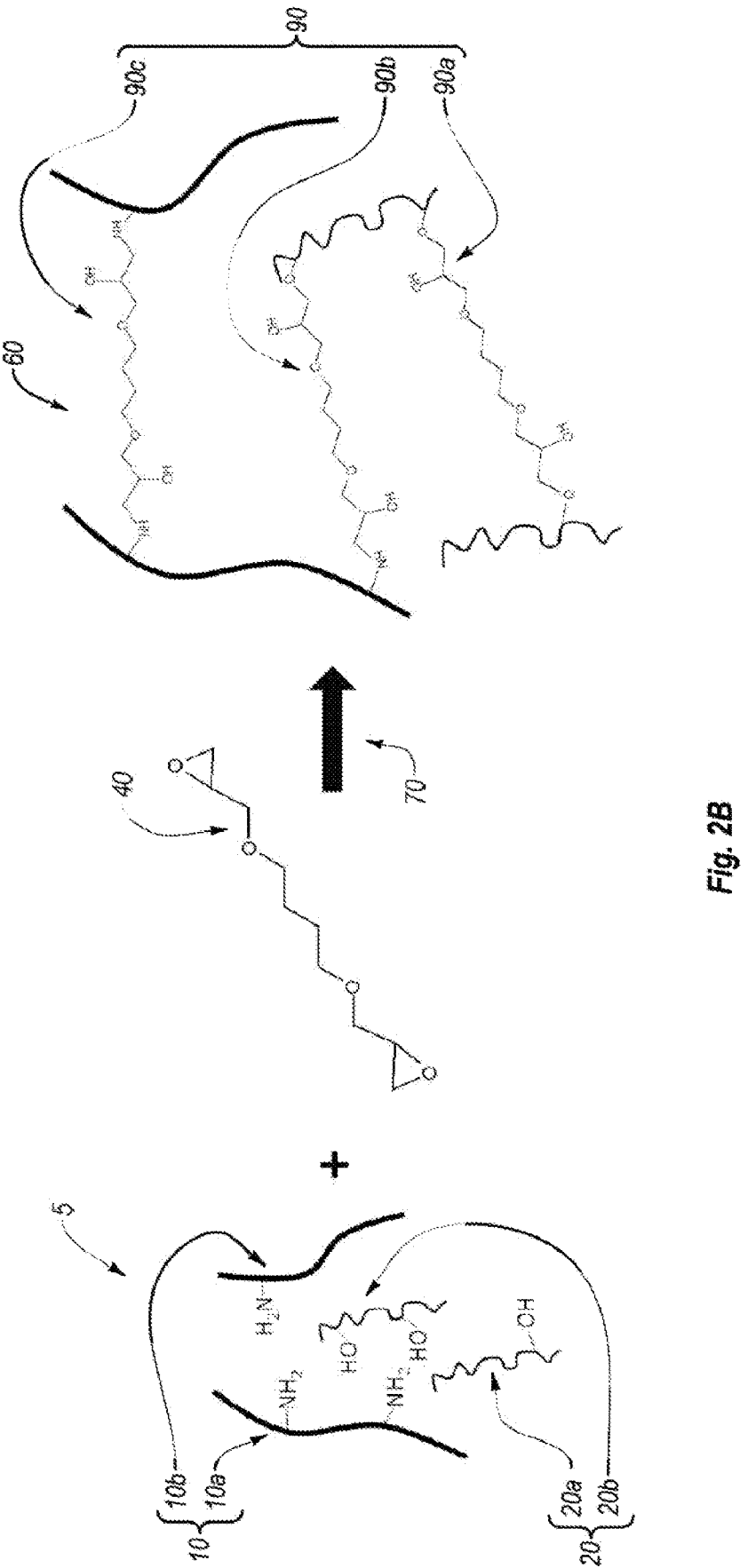
FIG. 2B illustrates another exemplary crosslinking reaction according to an embodiment of the present invention.

Referring now to FIG. 2B, some embodiments comprise one or more diol-containing bridges that are covalently bonded to a GAG by an ether bond and/or covalently bonded to a protein by a secondary amine bond. In one or more embodiments, diol-containing bridges can link: (i) a hydroxyl group of a GAG to an adjacent hydroxyl group of the same or different GAG; (ii) a hydroxyl group of a GAG to an adjacent amine group of an adjacent protein; or (iii) an amine group of a protein to an adjacent amine group of the same or different protein.

Some embodiments comprise one or more diol-containing bridges having between 3 and 12 carbon atoms. For instance, FIG. 2 illustrates crosslinked cartilage 50 having: (i) a butanediol bridge 90a between a hydroxyl group of a first GAG and a hydroxyl group of a second GAG; (ii) a butanediol bridge 90b between a hydroxyl group of a GAG and an amine group of a collagen fibril; and (iii) a butanediol bridge 90c between an amine group of a first collagen fibril and an amine group of a second collagen fibril. One will appreciate that in certain embodiments, reaction conditions can promote the formation of one or more specific type(s) of butanediol bridges 90. One will appreciate that, similar to the embodiment illustrated in FIG. 2A, one or more butanediol bridges between amine groups of the same collagen fibril and/or between hydroxyl groups of the same GAG molecule are also contemplated herein.

FIG. 2B also illustrates crosslinker 40. Crosslinker 40 can comprise a diol and/or an ether (e.g., 1,4 Butanediol diglycidyl ether or another reactive compound operable for generating one or more diol-containing bridges between molecules of cartilage 5). Some embodiments can include a combination of sulfone-containing bridges, diol-containing bridges (e.g., butanediol-bridges), and/or other carbon containing bridges, including bridges comprising a hydrocarbon diol having between 3 and 12 carbon atoms.

One will appreciate that the size, shape, and/or orientation, etc. of elements illustrated herein are not drawn to scale. Accordingly, such features should not be construed as limiting the scope of this disclosure or the invention described herein.

In some embodiments, the bridges comprise or occupy less than 20%, less than 19%, less than 18%, less than 17%, less than 16%, less than 15%, less than 10%, less than 5%, less than 2.5%, less than 1%, less than 0.1%, less than 0.01%, less than 0.001%, less than 0.0001%, between and 20%, between 0.001% and 15%, between 0.01% and 15%, between 0.01% and 10%, between 2.5% and 20%, between 0.01% and 2.5%, between 1% and 10%, and/or between 3% and 20% of the total number of potential bridges that could theoretically be introduced into the cartilage-derived implant based on the number of free hydroxyl and/or primary amines available to form bridges.

In at least one embodiment, the molecular bridge(s) present in the crosslinked cartilage (or cartilage-derived implant comprising crosslinked cartilage) provides resistance to enzymatic digestion. Accordingly, in some embodiments, the cartilage-derived implant is more resistant to enzymatic digestion than the source cartilage. As used herein, enzymatic "digestion" and similar terms can include enzymatic resorption and/or degradation. As used herein, enzymatic degradation can refer to the breaking of molecular bonds by an enzyme. Similarly, enzymatic resorption can refer to the degradation and subsequent assimilation of a compound or tissue. One will appreciate that, where appropriate, reference to one or more of enzymatic digestion, degradation, and/or resorption can imply and/or include other forms of enzymatic activity, including but not limited to digestion, degradation, and/or resorption.

As used herein, "resistant to enzymatic activity," "enzymatically resistant" and similar terms can refer to any statistically significant increase in resistance to or against enzymatic digestion compared to the source cartilage from which it was derived. In at least one embodiment, the cartilage-derived implant can exhibit a statistically significant (e.g., $p<0.05$) increase in stability against collagenase activity. One will appreciate, however, that other enzymes and/or forms of enzymatic activity are contemplated herein, including forms of enzymatic digestion of cartilage or component(s) thereof.

Figures 3A, 3B:
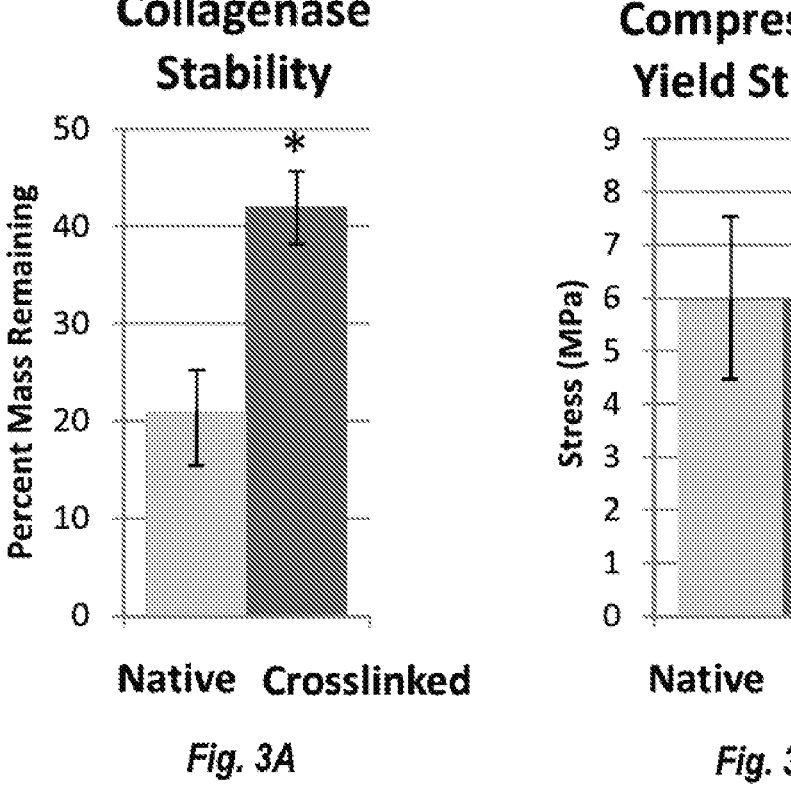
FIG. 3A illustrates an exemplary increase in collagenase stability following crosslinking treatment according to an embodiment of the present invention.
FIG. 3B illustrates an exemplary retention in compressive yield stress following crosslinking treatment according to an embodiment of the present invention.

As illustrated in FIG. 3A, native, unprocessed cartilage can retain only about 21% of the original mass subjected to a collagenase treatment assay. However, in the illustrated embodiment, processed, stabilized, and/or crosslinked cartilage (i.e., a cartilage-derived implant) can retain at least, up to, greater than, or approximately 42% of the original mass (of the native, source cartilage) subjected to a collagenase treatment assay ($p=0.01$). Thus, processed cartilage can retain approximately twice the mass than can native, unprocessed cartilage when subjected to a collagenase treatment assay. Similarly, processed cartilage can retain approximately 20% more mass than can native cartilage when exposed to collagenase.

One will appreciate, however, that in other embodiments, processed cartilage can retain less than 2 times or greater than 2 times, 3 times, 4 times, 5 times, or 10 times more mass than can native cartilage when exposed to collagenase. Similarly, processed cartilage can retain greater than 5%, 10%, 15%, 20%, 25%, 30%, 35%, 40%, 45%, 50%, 55%, 60%, 65%, 70%, 75%, 80%, 85%, 90%, 95%, 98%, or 99% of the original mass when exposed to collagenase. Likewise, processed cartilage can retain greater than 5%, 10%, 15%, 20%, 25%, 30%, 35%, 40%, 45%, 50%, 55%, 60%, 65%, 70%, 75%, 80%, 85%, 90%, 95%, 98%, or 99% more of the original mass than can native cartilage when exposed to collagenase.

One will also appreciate that in certain embodiments more rigorous and/or milder processing conditions can result in increased resistance to enzymatic digestion compared to the source cartilage. Processing conditions, as known in the art and described further below, can include reagent concentration(s), processing time(s), processing temperature(s), processing pH, level of agitation, presence or absence of additional reagents or processing steps, number of repeats for one or more steps, and/or other variables. Exemplary embodiments of some illustrative processing conditions, protocol, and results are discussed in further detail below.

In certain embodiments, the molecular bridge(s) or crosslinking provides resistance to enzymatic digestion while not significantly altering one or more biomechanical properties (e.g., strength) of the cartilage-derived implant relative to the source cartilage. Without being bound to theory, the introduction of too many bridges can change the mechanical properties of a cartilage-derived implant. For instance, the number of molecular bridges can influence the biomechanical (compressive yield) strength of the cartilage-derived implant. The number of molecular bridges can also influence the compressibility, compressive yield stress, compressive yield strain at break, elasticity, feel, Young's modulus, instantaneous stiffness, tensile strength, tensile strain, coefficient of friction, resilience, shock absorption, and/or other biomechanical properties of the cartilage-derived implant.

As illustrated in FIG. 3B, a processed, crosslinked, cartilage-derived implant can retain a comparable level of compressive yield strength (relative to the native, unprocessed, source cartilage). In the illustrated embodiment, native, non-crosslinked or non-stabilized, source cartilage has a compressive yield stress value of approximately 5.9 MPa (Std. Dev.=1.6) and processed, crosslinked cartilage has a compressive yield stress value of approximately 6.0 MPa (Std. Dev.=2.2). Thus, the compressive yield stress value of the processed, crosslinked cartilage falls within the range of the natural variation of the compressive yield stress value for the source cartilage or within a statistically relevant deviation or error value for the range of the natural variation of the compressive yield stress value for the source cartilage.

In some embodiments, the cartilage-derived implant can be resistant to cellular infiltration. For instance, upon implantation or assay conditions, the processed tissue can resist migration of cells from their sources of origin (e.g., during inflammations and/or cancerous growth). Without being bound to theory, cartilage and/or cartilaginous tissue is generally not conducive to cellular infiltration and is an inert structural material. Thus, in certain embodiments, the cartilage-derived implant can maintain the resistance to cellular infiltration present in native cartilage tissue. Furthermore, in some embodiments, the bridge(s) present in the cartilage-derived implant provide at least some protection from or resistance to or against molecular damage that can be caused by gamma or electron beam irradiation. Without being bound to theory, irradiation can weaken the biomechanical strength of cartilage and/or cartilaginous tissue (e.g., making the tissue less stiff by breaking molecular bonds). In at least one embodiment, crosslinking introduces new bonds that can help absorb the damage caused by irradiation. Thus, in certain embodiments, irradiated cartilage-derived implants can retain one or more biomechanical properties of the source cartilage (e.g., as a result of crosslinking).

In some embodiments, the cartilage-derived implant is sealed in a package that acts as a sterile barrier to the outside environment. In some embodiments the cartilage-derived implant is sterile with a sterility assurance level of at least, about, or less than $10^{-6}$, $10^{-5}$, $10^{-4}$, $10^{-3}$, or $10^{-2}$, where the sterility assurance level represents the probability of finding a non-sterile unit. In another embodiment, the cartilage-derived implant is produced from or by an aseptic process whereby the cartilage-derived implant possesses a sterility assurance level of $10^{-6}$, $10^{-5}$, $10^{-4}$, $10$, or $10^{-2}$.

Figure 4:
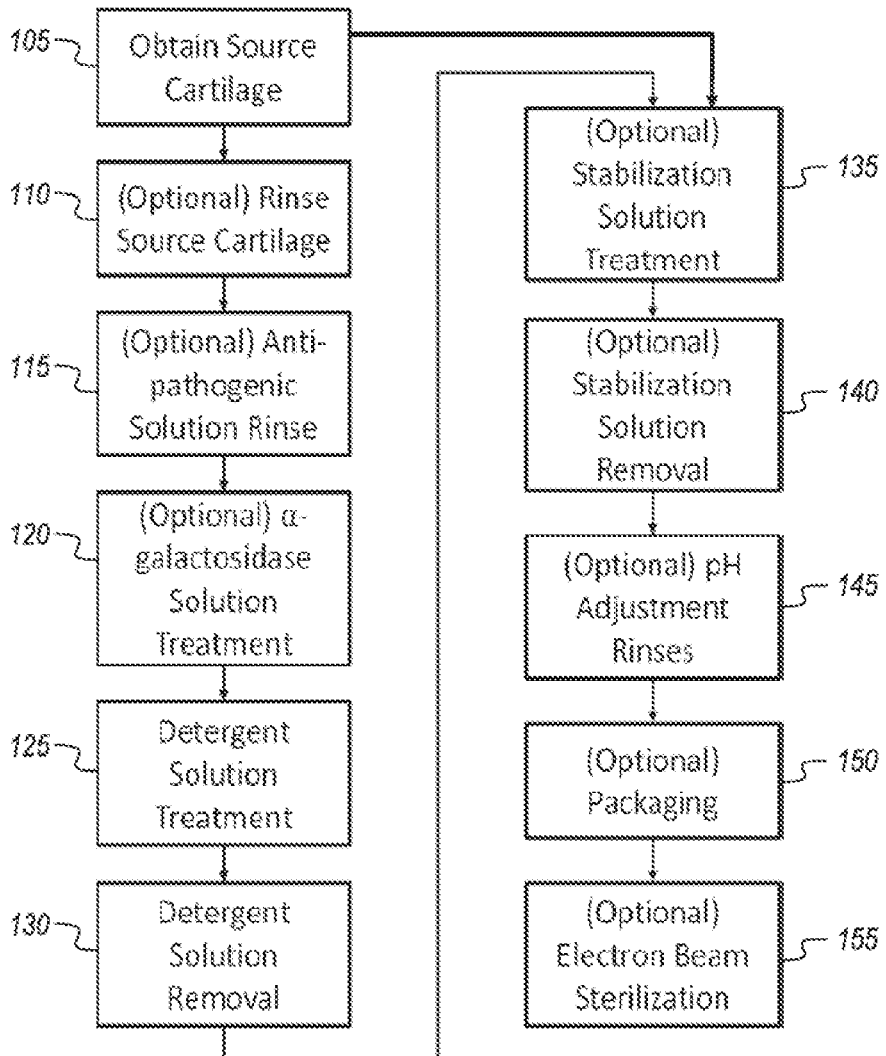
FIG. 4 illustrates an exemplary method of preparing a cartilage-derived implant according to an embodiment of the present invention.

Some embodiments include a method of processing animal-derived cartilage into a cartilage-derived implant (e.g., possessing one or more of the characteristics described above). Referring to FIG. 4, a method 100 can comprise a step 105 of obtaining a source cartilage and one or more optional steps, including: a step 110 of rinsing the cartilage (e.g., free or substantially free of blood and/or other component(s)); a step 115 of incubating the source cartilage in an antipathogenic solution; a step 120 of treating the source cartilage with a galactose-alpha-1,3-galactose removal solution; a step 125 of treating the source cartilage with a detergent solution comprising: (i) a cationic detergent solution; (ii) one or more additional detergents (e.g., anionic, nonionic or zwitterionic); (iii) one or more ionic, nonionic, or zwitterionic surfactants; and/or one or more nucleases and/or enzymes; a step 130 of removing the detergent solution; a step 135 of treating the cartilage with a stabilizing agent that forms bridges or crosslinks between collagen and GAG molecules; a step 140 of rinsing the cartilage free of unreacted stabilizing agent; a step 145 of rinsing the processed cartilage-derived implant (e.g., to adjust pH); a step 150 of packaging the cartilage-derived implant in a sealed package; and a step 155 of sterilizing the packaged cartilage-derived implant.

The source cartilage for the cartilage-derived implant can comprise septal, auricular, costal and/or articular cartilage from a pig, horse, cow, canine, human, or other animal. The animal can be a genetically modified animal that has been modified to exhibit certain genetic characteristics or advantages. For instance, in one embodiment, the source cartilage is derived from a non-primate animal genetically modified to lack or be deficient in galactose-alpha-1,3-galactose expression. In another embodiment, the source cartilage is derived from a non-human animal genetically modified to express one or more human proteins.

In one embodiment, the source cartilage can be recovered and/or cleaned (e.g., free or substantially free of surrounding tissue) and placed in a vessel. The vessel, as known in the art, can comprise a conical tube, flask, beaker, or sterile container. Optionally, the source cartilage can then be rinsed with a water, salt solution, or a buffer solution (e.g., to remove blood), illustratively for a period of 5 to 60 minutes and/or at a temperature between 1° C. and 40° C. with zero to three solution changes.

Optionally, the cartilage can then be incubated in an antipathogenic solution containing antibacterial, antifungal, and/or antiviral agents for a period of between 4 and 24 hours at a temperature between 20° C. and 40° C. with or without agitation. In some embodiments, the cartilage can then be incubated in a galactose-alpha-1,3-galactose removal solution containing a buffer (e.g. HEPES, phosphate, or Tris—having a pH between 3 and 9) and α-galactosidase enzyme for a period of between 4 and 24 hours at a temperature between 1° C. and 40° C. with or without agitation. Other enzymes that digest galactose-alpha-1,3-galactose can be used in place of α-galactosidase, such as endo-galactosidase C. In at least one embodiment, treatment with the enzyme(s) does not significantly digest GAGs present in cartilage. In some embodiments, the α-galactosidase can comprise a purified enzyme and/or a recombinant protein. In some embodiments, the α-galactosidase can be present in a concentration between 0.1 U/mL and 10 U/mL. In some embodiments, the pH of the galactose-alpha-1,3-galactose removal solution can be between 3 and 9.

Following recovery and/or any of the aforementioned optional steps (i.e., cleaning, antipathogenic treatment, and galactose-alpha-1,3-galactose removal solution treatment), the source cartilage can be incubated in a solution containing a cationic detergent (referred to as the detergent solution). In one embodiment, the detergent solution can comprise a quaternary ammonium compound (QAC). In one embodiment, the specific QAC is myristyltrimethylammonium bromide (aka tetradecyltrimethylammonium bromide or TTAB). In other embodiments, a different cationic detergent can be used. Examples of other cationic detergents that can be used include cetyltrimethylammonium bromide, tridodecylmethylammonium chloride, dodecyltrimethylammonium bromide, hexadecylpyridinium chloride, cetylpyridinium chloride, or benzyldodecyldimethylammonium bromide; however, it is understood that cationic detergents not listed here can also be used.

A combination of multiple cationic detergents can also be used in the detergent solution (rather than just one cationic detergent). Without being bound to theory, the detergent solution can be intended to kill any living cells and/or facilitate the removal of living cells and/or cellular remnants from the source cartilage. In some embodiments, cartilage can comprise a negatively charged tissue and, therefore, an oppositely charged detergent (e.g., a cationic detergent) can more easily diffuse through the source cartilage compared to a detergent containing a negative charge (anionic), no charge (non-ionic), or a net zero charge (zwitterionic). Therefore, in certain embodiments, a cationic detergent can have or provide an improved capability to cleanse the source cartilage of living cells and/or cellular remnants, compared to other detergents.

In some embodiments, the cationic detergent is present in the detergent solution at a concentration at, near, or above the critical micelle concentration (CMC) for that specific detergent. In other embodiments, the cationic detergent is present at or near a concentration two to twenty times less than the CMC for the specific detergent. In some embodiments, the detergent solution comprises a detergent concentration greater than 0.00111M and less than 25 mM.

Some embodiments include (the use of) a detergent solution comprising a non-detergent surfactant (e.g., in addition to the cationic detergent). In some embodiments, the surfactant aids in the removal of membrane associated proteins and/or galactose-alpha-1,3-galactose from the source cartilage. In at least one embodiment, the surfactant can be a non-detergent sulfobetaine (NDSB). In one aspect, the NDSB surfactant is 3-(1-Pyridino)-1-propane Sulfonate. In some embodiments, a different NDSB can be used, provided, and/or included. In some embodiments, the surfactant can facilitate the removal of cellular remnants.

Some embodiments include the addition of a nuclease to the cationic detergent solution. In some embodiments, the nuclease can comprise DNase and/or RNase, including combinations thereof. In other embodiments, the nuclease can comprise a *Serratia marcescens* derived nuclease such as Benzonase® or TurboNuclease. In other embodiments, the nuclease can comprise Cyanase™. One will appreciate, however, that generic, bio-equivalent, bio-identical, or structurally similar variations of such nucleases are also contemplate herein and/or can be included in certain embodiments. Without being bound to theory, the nuclease can be intended to facilitate the removal of RNA and/or DNA from the source cartilage. Some embodiments include the addition of antifungal agents to the detergent solution.

In some embodiments, the addition of antifungal agents to the detergent solution can reduce or eliminate the need for inclusion of a separate or additional anti-pathogenic solution treatment. One will also appreciate that other anti-microbial agents and treatments are contemplated herein.

In some embodiments, the detergent solution incubation step occurs with vigorous agitation. This agitation can induce a turbulent movement of detergent solution through or throughout at least a portion of the vessel. In some embodiments, the agitation occurs by vortexing, as known in the art. In other embodiments, the agitation can occur by shaking, rocking, and/or pressure mediated flow. The detergent solution incubation step can occur at a temperature between and 40° C., between 20° C. and 30° C., or between 33° C. and 40° C. In certain embodiments, a temperature closer to 40° C. may reduce the necessary incubation time. In some embodiments, the detergent solution incubation step occurs for between 1 and 30 hours, between 2 and 18 hours, between 8 and 24 hours or between 18 and 24 hours.

As discussed in further detail below, in some embodiments, the cationic detergent can have or provide the advantage of more effectively removing galactose-alpha-1,3-galactose and/or MHC proteins from the source cartilage compared to other non-cationic detergent washes. In one or more embodiments, QAC detergents can be or comprise antiseptic compounds that eliminate or reduce the need for (additional) antimicrobial (i.e., antifungal, antibiotic, and/or antiviral) reagents or treatments in or during processing. The detergent solution can also have or provide the advantage of cleansing the source cartilage while not significantly altering one or more biomechanical properties (e.g., strength) of the cartilage-derived implant relative to the source cartilage. The detergent solution can also or alternatively have or provide the advantage of cleansing the cartilage while not removing vital biochemical components of cartilage (e.g., GAGs and/or type II collagen).

In some embodiments, cationic detergent treatment can substantially reduce the amount of source organism DNA associated with the cartilage compared to the native, unprocessed cartilage. In at least one embodiment, treatment with a cationic detergent can remove essentially all of the source organism DNA from the cartilage. In other embodiments, treatment with a cationic detergent can remove all but a trace amount of source organism DNA from the cartilage. Furthermore, in at least one embodiment, within a relevant concentration range, decreasing concentrations of TTAB are progressively more effective in reducing source organism DNA. Furthermore, certain concentrations of cationic detergent can remove up to 99% of source organism DNA. In some embodiments, treatment with a cationic detergent can remove up to, at least, greater than, or approximately 25%, 50%, 75%, 80%, 85%, 90%, 91%, 92%, 93%, 94%, 95%, 96%, 97%, 98%, or 99% of source organism DNA (or living cells and/or cellular remnants).

In certain embodiments, the process of removing an amount of source organism DNA can occur without (the need for) one or more (additional) DNase, RNase, and/or enzyme reagents.

In some embodiments, treatment with a cationic detergent does not significantly alter or affect one or more biomechanical properties (e.g., compressive strength) of the cartilage-derived implant relative to the source cartilage. In at least one embodiment, treatment with a cationic detergent does not significantly alter or affect one or more of the compressibility, compressive yield stress, compressive yield strain at break, elasticity, feel, Young's modulus, instantaneous stiffness, tensile strength, tensile strain, coefficient of friction, resilience, shock absorption, and/or other biomechanical properties of the cartilage-derived implant. In at least one embodiment, treatment with a cationic detergent does not significantly alter or affect one or more biochemical properties (e.g., molecular composition) of the cartilage-derived implant relative to the source cartilage. In at least one embodiment, even relatively high concentrations and/or relatively long treatment times of cationic detergents can cleanse the cartilage sample without significantly altering one or more biomechanical properties.

Without being bound to theory, the processing of source cartilage (e.g., by treatment with one or more detergents, alcohols, or other reagents) can change the mechanical properties of a cartilage-derived implant. For instance, harsh detergents (e.g., anionic detergents, and some zwitterionic detergents) can influence the biomechanical (compressive yield) strength, compressibility, yield strain at break, elasticity, feel, Young's modulus, and/or other biomechanical properties of the cartilage-derived implant. In addition, alcohols can irreversibly dry and damage the cartilage by harming the molecular components and/or altering biochemical or biomechanical properties of the cartilage. Even mild detergents (e.g., non-ionic detergents, and some zwitterionic detergents) can damage cartilage with the prolonged exposure times and/or at high concentrations required to achieve the level of DNA (or living cells; cellular remnants; and/or galactose-alpha-1,3-galactose) reduction achieved in certain embodiments of the present invention.

In addition, anionic, zwitterionic, and non-ionic detergents may not remove living cells; cellular remnants; and/or galactose-alpha-1,3-galactose as effectively as one or more cationic detergents (e.g., at one or more concentrations, for a given period of time, at a given temperature, with or without agitation, and/or under one or more other reaction conditions). However, in some embodiments of the present invention, one or more non-cationic detergents can be included in the detergent solution (e.g., at a concentration below the CMC of that detergent). The low concentration of non-cationic detergent can also facilitate in the removal of certain cellular remnants in some embodiments of the present invention.

Following the detergent solution incubation, the source cartilage can be rinsed with a water, salt, or buffered salt solution in one to five successive steps or periods of between 15 and 240 minutes per period (e.g., at a temperature between 20 and 40° C. with or without agitation). In some embodiments, a rinse step is performed to remove detergents and surfactants from the cartilage-derived implant.

In some embodiments, the cartilage-derived implant (e.g., having been treated and optionally rinsed free of the detergent solution) can be treated with a stabilization solution. The stabilization solution can comprise a multifunctional reactive molecule that is configured to and/or capable of reacting with one or more hydroxyl and/or primary amine groups. In at least one embodiment, the multifunctional reactive molecule is or comprises divinyl sulfone (e.g., where the vinyl groups can react with one or more hydroxyl groups to form one or more ether bonds and/or the vinyl groups can react with one or more primary amine groups to form one or more secondary amine bonds). In another embodiment, the multifunctional reactive molecule is or comprises a di- or tri-epoxide (e.g., where the epoxide groups can react with one or more hydroxyl groups to form one or more ether bonds and/or the epoxide groups can react with one or more primary amine groups to form one or more secondary amine bonds). In some embodiments, the multi-functional epoxide is or comprises 1, 4 butanediol diglycidyl ether (BDDE). In other embodiments, the multi-functional epoxide is or comprises 1,2,7,8-Diepoxyoctane. One will appreciate, however, that other multi-functional epoxide are contemplated herein.

In some embodiments, the concentration of the multifunctional reactive molecule, the pH of the solution, the temperature of the reaction, and/or the length of incubation time can all affect the rate at which the multifunctional reactive molecule reacts to form bridges between cartilaginous molecules (e.g., to form the cartilage-derived implant). Illustratively, if too many molecular bridges are introduced, the cartilage-derived implant may not possess the benefit of maintaining a comparable mechanical strength and feel compared to the source cartilage. For instance, too many molecular bridges can influence the biomechanical (compressive yield) strength of the cartilage-derived implant, making the implant more brittle and less elastic than native cartilage. Accordingly, in certain embodiments, stabilization solution treatment, the formation of molecular bridge(s), and/or crosslinking does not significantly alter one or more biomechanical properties (e.g., strength) of the cartilage-derived implant relative to the source cartilage.

In some embodiments, treatment of the source cartilage with the stabilization solution occurs for a period of between 6 hours and 200 hours (e.g., at a temperature between 1° C. and 30° C. with or without agitation). In some embodiments the stabilization solution treatment step can be performed with agitation by vortexing, shaking, rocking, and/or pressure mediated flow.

In some embodiments the stabilization solution comprises a buffer that maintains the pH of the stabilization solution to a level greater than 9 and less than 12; or any value or range therebetween. In at least one embodiment, the pH of the reaction during treatment with stabilization solution can influence the number and/or type of molecular bridges formed and/or one or more mechanical properties of the resultant cartilage-derived implant. For instance, a processing pH value of 9 may result in a greater ratio of secondary amine bonds to ether bonds than a processing pH value of 12.

In some embodiments, the concentration of the multifunctional reactive molecule that reacts to form stabilizing bridges can be between 0.1 mM and 100 mM, 1 mM and 20 mM, 0.5 mM and 10 mM or 20 mM and 40 mM. Different combinations of temperature, incubation time, pH and concentration (within the ranges stated herein) can result in a cartilage-derived implant with the benefit of resistance to enzymatic digestion and/or maintenance of the source cartilage mechanical feel and/or (compressive yield) strength. For instance, in some embodiments, a higher concentration with a shorter reaction time can achieve a similar end result as a lower concentration with a longer reaction time.

In at least one embodiment, lower concentrations of the multifunctional reactive molecule can be used to form few molecular bridges or crosslinks. In some embodiments, the fewer crosslinks introduced into the sample, the more natural feel and/or other properties the implant retains. Accordingly, in certain embodiments fewer than 20% of the total available bridge-forming sites are crosslinked during stabilization treatment. In other embodiments, the less than 20%, less than 19%, less than 18%, less than 17%, less than 16%, less than 15%, less than 10%, less than 5%, less than 2.5%, less than 1%, less than 0.1%, less than 0.01%, less than 0.001%, less than 0.0001%, between 0.000001% and 20%, between 0.001% and 15%, between 0.01% and 15%, between 0.01% and 10%, between 2.5% and 20%, between 0.01% and 2.5%, between 1% and 10%, and/or between 3% and 20% of the total number of potential bridges that could theoretically be introduced into the cartilage-derived implant based on the number of free hydroxyl and/or primary amines available to form bridges are crosslinked during stabilization treatment.

In some embodiments, after treatment with the stabilization solution, the cartilage-derived implant can be rinsed (e.g., free or substantially free from unreacted multifunctional reactive molecules; e.g., with or in a buffer that maintains the pH to a level greater than 9 and less than 12). In some embodiments the post stabilization rinse can comprise one to five successive rinse steps or periods (e.g., of between and 15 and 2000 minutes per period, at a temperature between 20° C. and 30° C., and/or with or without agitation). In some embodiments, the post stabilization rinse permits or allows for a continuation of stabilization or bridge formation for reactive molecules in which only one end has reacted with a GAG or protein. In some embodiments, the stabilization rinse comprises a buffer that maintains the pH to a level greater than 9 and less than 12 and an additional primary amine-containing solute. In some embodiments, the solute comprises an amino acid (e.g., glycine). In some embodiments, the amine containing solute can react with a free reactive group that has not yet formed a bridge in the cartilage-derived implant.

In certain embodiments, the formation of one or more molecular bridges provides the cartilage-derived implant with resistance to enzymatic digestion. Accordingly, in some embodiments, the stabilization solution treatment makes the cartilage-derived implant resistant to enzymatic digestion. In at least one embodiment, stabilization solution treatment, the formation of molecular bridge(s), and/or crosslinking makes the cartilage-derived implant resistant to enzymatic digestion and does not significantly alter one or more biomechanical properties (e.g., strength) of the cartilage-derived implant relative to the source cartilage.

In some embodiments, treatment with the stabilization solution makes the cartilage-derived implant less susceptible to damage by electron beam and/or gamma radiation. One will appreciate that the stabilization solution treatment and/or high pH buffer rinse(s) can be performed or utilized on a cartilage-based implant that has not been first treated with the detergent solution described above. Thus, the stabilization solution treatment can comprise a standalone treatment or method of producing a cartilage-derived implant (e.g., that has been stabilized with molecular bridges, possesses the benefits of resistance to enzymatic resorption and/or protection from radiation-induced damage, and/or is mechanically comparable in feel and/or strength compared to the source cartilage material).

Following the optional high pH buffer rinse, the cartilage-derived implant can be rinsed with an isotonic saline and/or buffered saline solution (e.g., having a pH of between 5 and 8; or any value or range therebetween). The rinse step can comprise one to five successive steps or periods of rinsing (e.g., between and 15-240 minutes per period, at a temperature between 20° C. and 30° C., and/or with or without agitation). With this step, the cartilage-derived implant is brought to a more physiologically relevant pH level.

In some embodiments, the cartilage-derived implant can be sealed in a package. In at least one embodiment, the package can safely withstand electron beam and/or gamma irradiation treatment. In some embodiments, the cartilage-derived implant can be packaged together with at least some residual solution. For instance, the cartilage-derived implant can be packaged together with less than 1 mL of solution. In some embodiments, the solution can comprise isotonic saline and/or buffered saline. In other embodiments the cartilage-derived implant can be sealed in a package with between 1 and 10 mL of additional solution. In other embodiments, the cartilage-derived implant is sealed in a package with no additional solution added. In at least one embodiment, the cartilage-derived implant can be packaged together with at least a trace amount of (or at least some residual) detergent (e.g., cationic detergent), surfactant, enzyme, multifunctional reactive molecule, and/or other reagent or component described herein.

In some embodiments, the packaged cartilage-derived implant can be sterilized by electron beam and/or gamma irradiation. Without being bound to theory, both forms of radiation sterilization are known to degrade or break the molecular bonds of the GAGs and/or collagen of cartilage, which can cause a change in the mechanical stiffness of the cartilage-derived implant. In at least one embodiment, electron beam irradiation can provide an advantage of requiring shorter exposure time compared to gamma irradiation. In another embodiment, electron beam irradiation can result in reduced degradation of GAGs and/or collagen, and/or reduced change in mechanical stiffness of the cartilage-derived implant. In another aspect (electron beam or gamma) sterilization can occur at a temperature between $-20°$ C. and $-80°$ C. (e.g., about $-40°$ C.). In some embodiments, performing sterilization at a colder temperature can further reduce breakage of GAGs and further reduces changes of mechanical stiffness. In one embodiment the total dose of electron beam irradiation received by the implant can be between 1 and 20 kGy. In another embodiment, the total dose of electron beam irradiation received by the implant can be between 6 and 18 kGy.

The invention also relates to methods of use for a cartilage-derived implant. In some embodiments, the cartilage-derived implant is used for repairing or reconstructing cartilaginous structures. In some embodiments, the method comprises obtaining a cartilage-derived implant (e.g., as described herein), sculpting the cartilage-derived implant into a specific shape, and/or implanting the cartilage-derived implant into the nose, ear, articular joint, or other anatomical location requiring repair with a cartilage-derived implant. In another embodiment, the method comprises obtaining the cartilage-derived implant, shaping the cartilage-derived implant to fit the shape of a cartilage defect, and/or implanting the cartilage-derived implant into the defect site. In one embodiment, a cartilage-derived implant whose source cartilage is septal cartilage can be shaped and/or implanted in the course of a rhinoplasty procedure.

Without being bound by theory, whereas other allograft derived materials can resorb over time, certain cartilage-derived implants described herein can provide resistance to enzymatic resorption. Likewise, whereas synthetic-derived materials used in rhinoplasty may extrude over time, some cartilage-derived implants described herein, being a natural material, can be resistant to extrusion. Likewise, whereas traditional costal cartilage grafts used in rhinoplasty may warp over time due to internal graft stresses, enzymatic resorption, or fibrous deposition, some cartilage-derived implants described herein can be resistant to enzymatic resorption and, by nature of being the same type of cartilage as the repaired, replaced, or augmented cartilage, can be less likely to elicit excess fibrous tissue deposition over time or experience unnatural stresses.

The following examples represent exemplary embodiments and are provided for illustrative purposes only. Accordingly, the disclosed examples are meant to illustrate one or more aspects of the invention and are not intended to limit the scope of the present invention.

Example 1: An Exemplary Cartilage-Derived Implant

One embodiment comprising a cartilage-derived implant can be produced as follows. Septal cartilage from a pig is collected, dissected free of surrounding tissues, cut to dimensions of 2 cm×6 cm, and then placed in a 50 mL container (e.g., tube) along with 45 mL of isotonic saline. The container is placed on a tube shaker and allowed to shake at 400 RPM for 15 minutes. After 15 minutes, the rinsate is removed from the container and replaced with 45 mL of various cationic detergent solutions (see Table 1 below). Detergents and surfactants used in these processes are listed below in Table 1 and include the following: Tetradecyltrimethylammonium bromide (TTAB), Cetyltrimethylammonium bromide (CTAB), 3-(1-Pyridino)-1-propane Sulfonate (NDSB 201), and Dimethylbenzylammonium Propane Sulfonate (NDSB 256). The container is then incubated at either 25° C. or 37° C. with high speed vortexing agitation for 24 hours. After 24 hours, the detergent solution is removed and replaced with 45 mL of isotonic saline. The container is incubated at 25° C. with high speed vortexing agitation for five successive rinses of 1 hour each with the isotonic saline being changed between each rinse.

TABLE 1

| ID | Buffer | Nuclease | Detergent | Detergent Conc., mM | Surfactant | Surfactant Conc., % w/v | pH | Temp, ° C. |
|---|---|---|---|---|---|---|---|---|
| 1 | PBS | none | TTAB | 4 | none | — | 7.4 | 37 |
| 2 | PBS | none | CTAB | 1 | none | — | 7.4 | 37 |
| 3 | PBS | none | TTAB | 4 | NDSB 201 | 0.5 | 7.4 | 37 |
| 4 | PBS | none | CTAB | 1 | NDSB 201 | 0.5 | 7.4 | 37 |
| 5 | PBS | none | TTAB | 4 | NDSB 256 | 0.5 | 7.4 | 37 |
| 6 | PBS | none | CTAB | 1 | NDSB 256 | 0.5 | 7.4 | 37 |

TABLE 1-continued

| ID | Buffer | Nuclease | Detergent | Detergent Conc., mM | Surfactant | Surfactant Conc., % w/v | pH | Temp, ° C. |
|---|---|---|---|---|---|---|---|---|
| 7 | PBS | none | TTAB | 4 | NDSB 201 | 0.1 | 7.4 | 37 |
| 8 | PBS | none | CTAB | 1 | NDSB 201 | 0.1 | 7.4 | 37 |
| 9 | PBS | none | TTAB | 4 | NDSB 256 | 0.1 | 7.4 | 37 |
| 10 | PBS | none | CTAB | 1 | NDSB 256 | 0.1 | 7.4 | 37 |
| 11 | 50 mM Tris, 2 mM Mg | Benzonase ® | TTAB | 4 | none | — | 8 | 37 |
| 12 | 50 mM Tris, 2 mM Mg | Benzonase ® | CTAB | 1 | none | — | 8 | 37 |
| 13 | 50 mM Tris, 2 mM Mg | Benzonase ® | TTAB | 4 | NDSB 201 | 0.5 | 8 | 37 |
| 14 | 50 mM Tris, 2 mM Mg | Benzonase ® | CTAB | 1 | NDSB 201 | 0.5 | 8 | 37 |
| 15 | 50 mM Tris, 2 mM Mg | Benzonase ® | TTAB | 4 | NDSB 256 | 0.5 | 8 | 37 |
| 16 | 50 mM Tris, 2 mM Mg | Benzonase ® | CTAB | 1 | NDSB 256 | 0.5 | 8 | 37 |
| 17 | 50 mM Tris, 2 mM Mg | Benzonase ® | TTAB | 4 | NDSB 201 | 0.1 | 8 | 37 |
| 18 | 50 mM Tris, 2 mM Mg | Benzonase ® | CTAB | 1 | NDSB 201 | 0.1 | 8 | 37 |
| 19 | 50 mM Tris, 2 mM Mg | Benzonase ® | TTAB | 4 | NDSB 256 | 0.1 | 8 | 37 |
| 20 | 50 mM Tris, 2 mM Mg | Benzonase ® | CTAB | 1 | NDSB 256 | 0.1 | 8 | 37 |
| 21 | 50 mM Tris, 6 mM Mn | Cyanase ™ | TTAB | 4 | none | — | 8 | 37 |
| 22 | 50 mM Tris, 6 mM Mn | Cyanase ™ | CTAB | 1 | none | — | 8 | 37 |
| 23 | 50 mM Tris, 6 mM Mn | Cyanase ™ | TTAB | 4 | NDSB 201 | 0.5 | 8 | 37 |
| 24 | 50 mM Tris, 6 mM Mn | Cyanase ™ | CTAB | 1 | NDSB 201 | 0.5 | 8 | 37 |
| 25 | 50 mM Tris, 6 mM Mn | Cyanase ™ | TTAB | 4 | NDSB 256 | 0.5 | 8 | 37 |
| 26 | 50 mM Tris, 6 mM Mn | Cyanase ™ | CTAB | 1 | NDSB 256 | 0.5 | 8 | 37 |
| 27 | 50 mM Tris, 6 mM Mn | Cyanase ™ | TTAB | 4 | NDSB 201 | 0.1 | 8 | 37 |
| 28 | 50 mM Tris, 6 mM Mn | Cyanase ™ | CTAB | 1 | NDSB 201 | 0.1 | 8 | 37 |
| 29 | 50 mM Tris, 6 mM Mn | Cyanase ™ | TTAB | 4 | NDSB 256 | 0.1 | 8 | 37 |
| 30 | 50 mM Tris, 6 mM Mn | Cyanase ™ | CTAB | 1 | NDSB 256 | 0.1 | 8 | 37 |
| 31 | PBS | none | TTAB | 4 | none | — | 7.4 | 25 |
| 32 | PBS | none | CTAB | 1 | none | — | 7.4 | 25 |
| 33 | PBS | none | TTAB | 4 | NDSB 201 | 0.5 | 7.4 | 25 |
| 34 | PBS | none | CTAB | 1 | NDSB 201 | 0.5 | 7.4 | 25 |
| 35 | PBS | none | TTAB | 4 | NDSB 256 | 0.5 | 7.4 | 25 |
| 36 | PBS | none | CTAB | 1 | NDSB 256 | 0.5 | 7.4 | 25 |
| 37 | PBS | none | TTAB | 4 | NDSB 201 | 0.1 | 7.4 | 25 |
| 38 | PBS | none | CTAB | 1 | NDSB 201 | 0.1 | 7.4 | 25 |
| 39 | PBS | none | TTAB | 4 | NDSB 256 | 0.1 | 7.4 | 25 |
| 40 | PBS | none | CTAB | 1 | NDSB 256 | 0.1 | 7.4 | 25 |
| 41 | 50 mM Tris, 2 mM Mg | Benzonase ® | TTAB | 4 | none | — | 8 | 25 |
| 42 | 50 mM Tris, 2 mM Mg | Benzonase ® | CTAB | 1 | none | — | 8 | 25 |
| 43 | 50 mM Tris, 2 mM Mg | Benzonase ® | TTAB | 4 | NDSB 201 | 0.5 | 8 | 25 |
| 44 | 50 mM Tris, 2 mM Mg | Benzonase ® | CTAB | 1 | NDSB 201 | 0.5 | 8 | 25 |
| 45 | 50 mM Tris, 2 mM Mg | Benzonase ® | TTAB | 4 | NDSB 256 | 0.5 | 8 | 25 |

TABLE 1-continued

| ID | Buffer | Nuclease | Detergent | Detergent Conc., mM | Surfactant | Surfactant Conc., % w/v | pH | Temp, ° C. |
|---|---|---|---|---|---|---|---|---|
| 46 | 50 mM Tris, 2 mM Mg | Benzonase ® | CTAB | 1 | NDSB 256 | 0.5 | 8 | 25 |
| 47 | 50 mM Tris, 2 mM Mg | Benzonase ® | TTAB | 4 | NDSB 201 | 0.1 | 8 | 25 |
| 48 | 50 mM Tris, 2 mM Mg | Benzonase ® | CTAB | 1 | NDSB 201 | 0.1 | 8 | 25 |
| 49 | 50 mM Tris, 2 mM Mg | Benzonase ® | TTAB | 4 | NDSB 256 | 0.1 | 8 | 25 |
| 50 | 50 mM Tris, 2 mM Mg | Benzonase ® | CTAB | 1 | NDSB 256 | 0.1 | 8 | 25 |
| 51 | 50 mM Tris, 6 mM Mn | Cyanase ™ | TTAB | 4 | none | — | 8 | 25 |
| 52 | 50 mM Tris, 6 mM Mn | Cyanase ™ | CTAB | 1 | none | — | 8 | 25 |
| 53 | 50 mM Tris, 6 mM Mn | Cyanase ™ | TTAB | 4 | NDSB 201 | 0.5 | 8 | 25 |
| 54 | 50 mM Tris, 6 mM Mn | Cyanase ™ | CTAB | 1 | NDSB 201 | 0.5 | 8 | 25 |
| 55 | 50 mM Tris, 6 mM Mn | Cyanase ™ | TTAB | 4 | NDSB 256 | 0.5 | 8 | 25 |
| 56 | 50 mM Tris, 6 mM Mn | Cyanase ™ | CTAB | 1 | NDSB 256 | 0.5 | 8 | 25 |
| 57 | 50 mM Tris, 6 mM Mn | Cyanase ™ | TTAB | 4 | NDSB 201 | 0.1 | 8 | 25 |
| 58 | 50 mM Tris, 6 mM Mn | Cyanase ™ | CTAB | 1 | NDSB 201 | 0.1 | 8 | 25 |
| 59 | 50 mM Tris, 6 mM Mn | Cyanase ™ | TTAB | 4 | NDSB 256 | 0.1 | 8 | 25 |
| 60 | 50 mM Tris, 6 mM Mn | Cyanase ™ | CTAB | 1 | NDSB 256 | 0.1 | 8 | 25 |

Example 2: Stabilization Solution Treatment with a Multifunctional Reactive Molecule In one embodiment, a cartilage-derived implant produced in Example 1 is further processed with a stabilization solution to impart the benefits of stabilization. The cartilage-derived implant produced in Example 1 is placed in a 50 ml container with 45 mL of stabilization solution comprising 5 mM BDDE in a 100 mM bicarbonate buffer, pH 11. The container is placed on a tube shaker and allowed to shake at 300 RPM for 24 hours at 25 C. After 24 hours the stabilization solution is removed and replaced with 45 mL of 100 mM bicarbonate buffer pH 11. The container is incubated at 25° C. with shaking at 1000 RPM for three successive rinses of 15 minutes, 1 hour, and 24 hours, respectively, with the buffer solution being changed between each rinse. Following the buffer rinses, the buffer is replaced with 45 mL of 50 mM Tris-buffered saline, pH 7.4. The container is incubated at 25° C. with shaking at 300 RPM for three successive rinses of 15 minutes each with the Tris-buffered saline being changed between each rinse.

Example 3: Packaging and Terminal Sterilization

Another exemplary embodiment relates to terminal sterilization of the cartilage-derived implant. In this example, the cartilage-derived implant from Example 1 or 2 is placed in a plastic container and sealed to form a sterile barrier between the cartilage-derived implant and the outside environment. The cartilage-derived implant is then placed into a box containing dry ice and then transported to an electron beam facility, if necessary. The cartilage-derived implant is irradiated with one side of the graft against the dry ice and the other side in direct exposure to the electron beam source. The cartilage-derived implant is then exposed to 8-12 kGy of irradiation.

Example 4: DNA Quantification Assay 100 mg samples were cut to fine pieces with a scalpel and digested in 1.5 mL of 0.5 mg/mL Proteinase K in 10×PBS with 5 mM EDTA for 4 hr at 55° C. with constant shaking. Sample digestions were then quantified using the Quant-iT™ High-Sensitivity DNA Assay Kit by Life Technologies (Carlsbad, CA).

Example 5: DNA Reduction in Cationic Detergent Treated Cartilage

Figure 5:
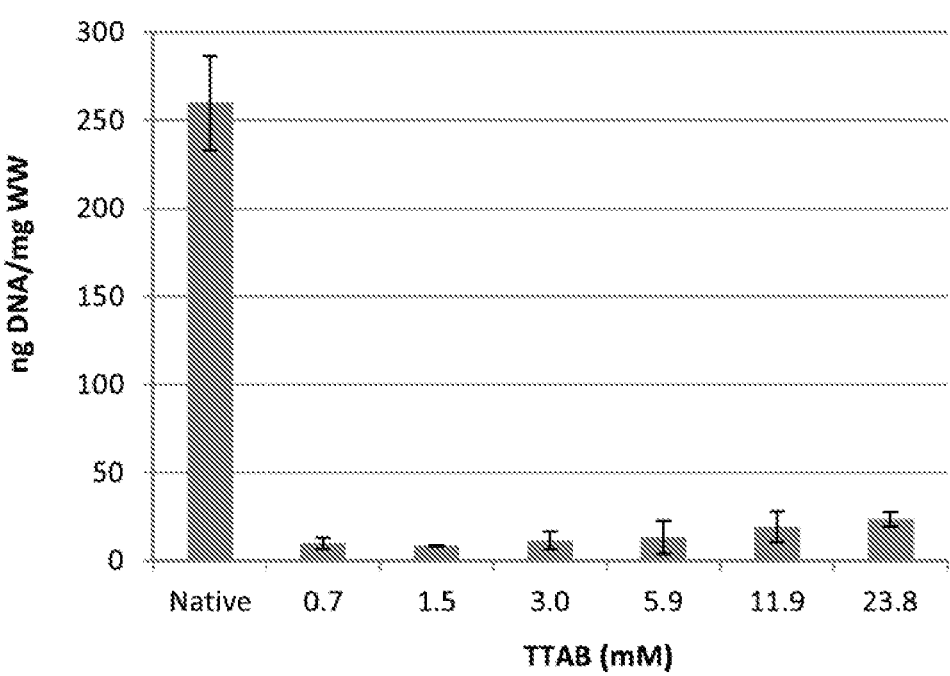
FIG. 5 illustrates an exemplary series of reductions in residual DNA following cationic detergent treatment according to an embodiment of the present invention.
Figure 6:
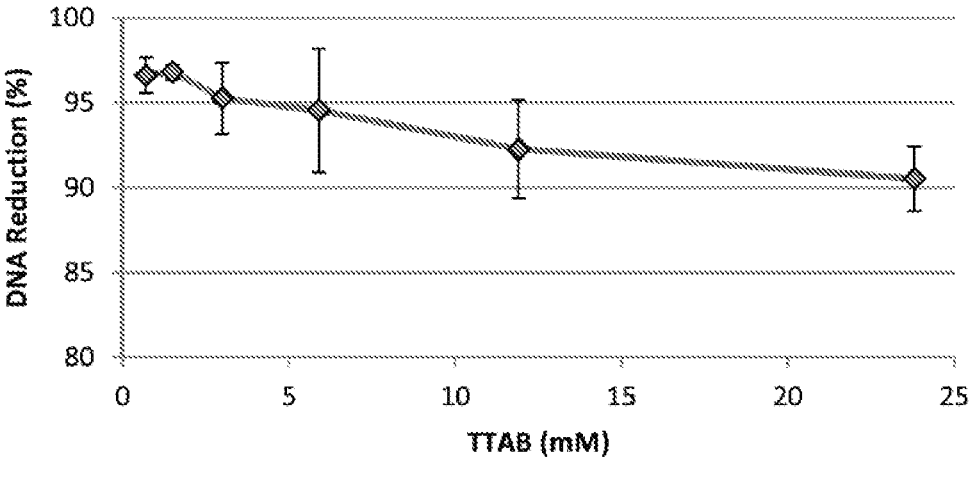
FIG. 6 illustrates an exemplary series of percent reduction in DNA content following cationic detergent treatment according to an embodiment of the present invention.

As illustrated in FIG. 5, and corresponding Tables 2 and 3, varying concentrations of TTAB can remove varying amounts of source organism DNA. In summary, while native porcine septal cartilage contains greater than about 250 ng DNA per mg wet weight cartilage, cationic detergent treated cartilage-derived implants can comprise less than or between about 8.6 and about ng DNA per mg wet weight cartilage. Similarly, FIG. 6, and corresponding Tables 2 and 3, illustrate percent reduction in source organism DNA following treatment with varying amounts of TTAB. In summary, within a relevant concentration range, decreasing concentrations of TTAB are progressively more effective in reducing source organism DNA. At lower concentrations, for instance, TTAB treatment effectively removes greater than 96% of source organism DNA from the cartilage-derived implant.

Table 2 displays the average values of percent DNA reduction and residual DNA amount for each of the tested concentrations of TTAB. Table 3 displays the replicate data for each tested concentration from which the averages were derived.

TABLE 2

| | TTAB Conc. (mM) | DNA Reduction (%) | Std Dev | DNA (ng/mg WW) | Std Dev | ttest vs. Native |
|---|---|---|---|---|---|---|
| Processed | 23.8 | 90.5 | 1.9 | 23.8 | 4.1 | 1.35E−12 |
| | 11.9 | 92.3 | 2.9 | 19.4 | 8.6 | 1.37E−12 |
| | 5.9 | 94.5 | 3.7 | 13.3 | 9.3 | 1.01E−12 |
| | 3.0 | 95.3 | 2.1 | 11.7 | 5.1 | 4.14E−16 |
| | 1.5 | 96.8 | 0.4 | 8.6 | 0.3 | 2.11E−09 |
| | 0.7 | 96.6 | 1.0 | 9.8 | 3.0 | 2.26E−09 |
| Native | 0.0 | 0.0 | 0.0 | 259.7 | 26.7 | 1.00E+00 |

TABLE 3

| TTAB (mM) | Porcine Source ID | DNA (ng/mg Wet Weight) | % DNA Reduction (relative to same Porcine Source) |
|---|---|---|---|
| (Native) | a1 | 270.5 | 0 |
| (Native) | b1 | 232.8 | 0 |
| (Native) | c1 | 234.8 | 0 |
| (Native) | d1 | 250.8 | 0 |
| (Native) | e1 | 255.6 | 0 |
| (Native) | a4 | 263.5 | 0 |
| (Native) | b4 | 295.8 | 0 |
| (Native) | c4 | 231.7 | 0 |
| (Native) | d4 | 266.5 | 0 |
| (Native) | e4 | 240.1 | 0 |
| (Native) | f4 | 314.8 | 0 |
| | Average | 259.7 | 0.0 |
| | Std Dev | 26.69 | 0.00 |
| 23.8 | a1 | 19.9 | 92.6 |
| 23.8 | b1 | 19.2 | 91.8 |
| 23.8 | e1 | 26.5 | 89.6 |
| 23.8 | a1 | 21.4 | 92.1 |
| 23.8 | b1 | 28.0 | 88.0 |
| 23.8 | e1 | 27.9 | 89.1 |
| | Average | 23.8 | 90.5 |
| | Std Dev | 4.11 | 1.89 |
| 11.9 | a1 | 23.5 | 91.3 |
| 11.9 | b1 | 10.2 | 95.6 |
| 11.9 | c1 | 19.8 | 91.6 |
| 11.9 | a1 | 33.9 | 87.5 |
| 11.9 | b1 | 12.1 | 94.8 |
| 11.9 | c1 | 16.8 | 92.8 |
| | Average | 19.4 | 92.3 |
| | Std Dev | 8.61 | 2.91 |
| 5.9 | d1 | 22.8 | 90.9 |
| 5.9 | b1 | 2.2 | 99.1 |
| 5.9 | c1 | 13.5 | 94.2 |
| 5.9 | d1 | 25.5 | 89.8 |
| 5.9 | b1 | 5.6 | 97.6 |
| 5.9 | c1 | 10.2 | 95.6 |
| | Average | 13.3 | 94.5 |
| | Std Dev | 9.31 | 3.65 |
| 3.0 | d1 | 10.9 | 95.6 |
| 3.0 | e1 | 19.1 | 92.5 |
| 3.0 | c1 | 8.5 | 96.4 |
| 3.0 | d1 | 11.8 | 95.3 |
| 3.0 | e1 | 12.0 | 95.3 |
| 3.0 | c1 | 6.6 | 97.2 |
| 3.0 | a4 | 12.7 | 95.2 |
| 3.0 | e4 | 4.2 | 98.3 |
| 3.0 | c4 | 19.6 | 91.6 |
| | Average | 11.7 | 95.3 |
| | Std Dev | 5.15 | 2.10 |
| 1.5 | a4 | 8.9 | 96.6 |
| 1.5 | e4 | 8.3 | 96.5 |
| 1.5 | f4 | 8.5 | 97.3 |
| | Average | 8.6 | 96.8 |
| | Std Dev | 0.29 | 0.41 |
| 0.74 | a4 | 10.7 | 95.9 |
| 0.74 | b4 | 6.5 | 97.8 |

TABLE 3-continued

| TTAB (mM) | Porcine Source ID | DNA (ng/mg Wet Weight) | % DNA Reduction (relative to same Porcine Source) |
|---|---|---|---|
| 0.74 | f4 | 12.3 | 96.1 |
| | Average | 9.8 | 96.6 |
| | Std Dev | 3.03 | 1.04 |

Example 6: Galactose-Alpha-1,3-Galactose Competitive ELISA

An ELISA plate was prepared by coating with 50 µL of 10 µg/mL BSA-alpha gal (Dextra Laboratories, UK) in TBS incubating overnight at 4° C. The plate was then washed 3 times with PBS, blocked for 1 hr at 37° C. with 150 µL of 1.5% HSA, and then washed again 3 times with PBS. 100 mg samples were minced and incubated in a 1:100 M86 antibody (Enzo Life Sciences, Farmingdale, NY) solution in PBS overnight at 4° C. with slight shaking. Rabbit red blood cells known to possess $2 \times 10^6$ alpha-gal epitopes per cell were also incubated in a 1:100 antibody solution at various concentrations to create a standard curve. Samples and standards were centrifuged at 20,000 g at 4° C. for 30 minutes and 50 µL of the supernatant for each sample and standard were loaded into wells of the prepared plate in triplicate. After a 2 hr room temperature incubation, the plate was washed and incubated for 1 hr with a hrp-conjugated goat anti-mouse antibody (1:500 in PBS). The plate was washed again, exposed for 15 minutes with 50 µL of a TMB substrate and stopped with 50 µL of a 0.2M sulfuric acid solution. The absorbance of each well at 450 nm was measured by a plate reader.

Figure 7:
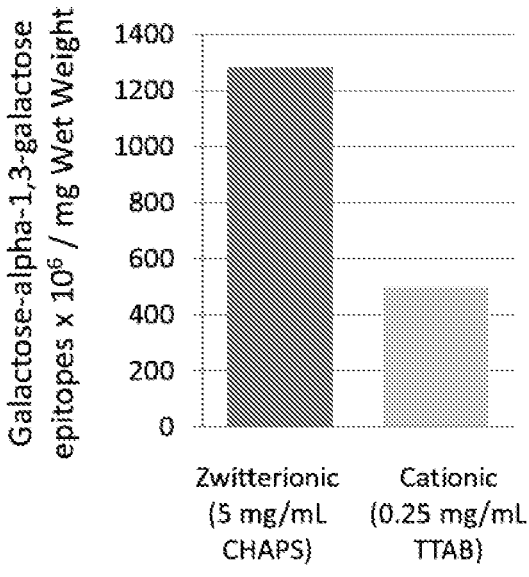
FIG. 7 illustrates exemplary residual galactose-alpha-1, 3-galactose following cationic and zwitterionic detergent treatment according to an embodiment of the present invention.

Example 7: Galactose-Alpha-1,3-Galactose Reduction in Cationic Detergent Treated Cartilage As illustrated in FIG. 7, and corresponding Table 4, cationic detergent can remove more galactose-alpha-1,3-galactose from the source cartilage than can zwitterionic detergent. In summary, while native source cartilage treated with 5 mg/mL CHAPS retains $1.281 \times 10^9$ galactose-alpha-1,3-galactose epitopes per mg wet weight cartilage, native source cartilage treated with 0.25 mg/mL TTAB retains only $4.97 \times 10^8$ galactose-alpha-1,3-galactose epitopes per mg wet weight cartilage. Thus, zwitterionic detergent treated cartilage retains greater than twice as much residual galactose-alpha-1,3-galactose than does cationic detergent treated cartilage. Similarly, cationic detergent treated cartilage can retain up to, greater than, or about 50% less galactose-alpha-1,3-galactose (or other immunogenic protein or effector) than does cartilage treated with zwitterionic detergent. Table 4 displays the values of galactose-alpha-1,3-galactose epitopes remaining after detergent treatment at the indicated concentrations of CHAPS and TTAB, respectively.

TABLE 4

| Detergent Type | Treatment | Epitopes per mg Wet Weight (×10^6) |
|---|---|---|
| Zwitterionic | CHAPS (5 mg/mL) | 1,281 |

TABLE 4-continued

| Detergent Type | Treatment | Epitopes per mg Wet Weight (×10^6) |
|---|---|---|
| Cationic | TTAB (0.25 mg/mL) | 497 |

Example 8: Biomechanics as Say

Two 6 mm circular disks were obtained from each sample and the thickness of each disk was cut to ~4 mm with a scalpel. After a tare load of 10N was placed on a disk, the disk was rapidly compressed in an unconfined compression using an Instron Mini 55 and 500N load cell at a rate of 3 mm/s to a stopping point of 85% compressive strain.

Figure 8:
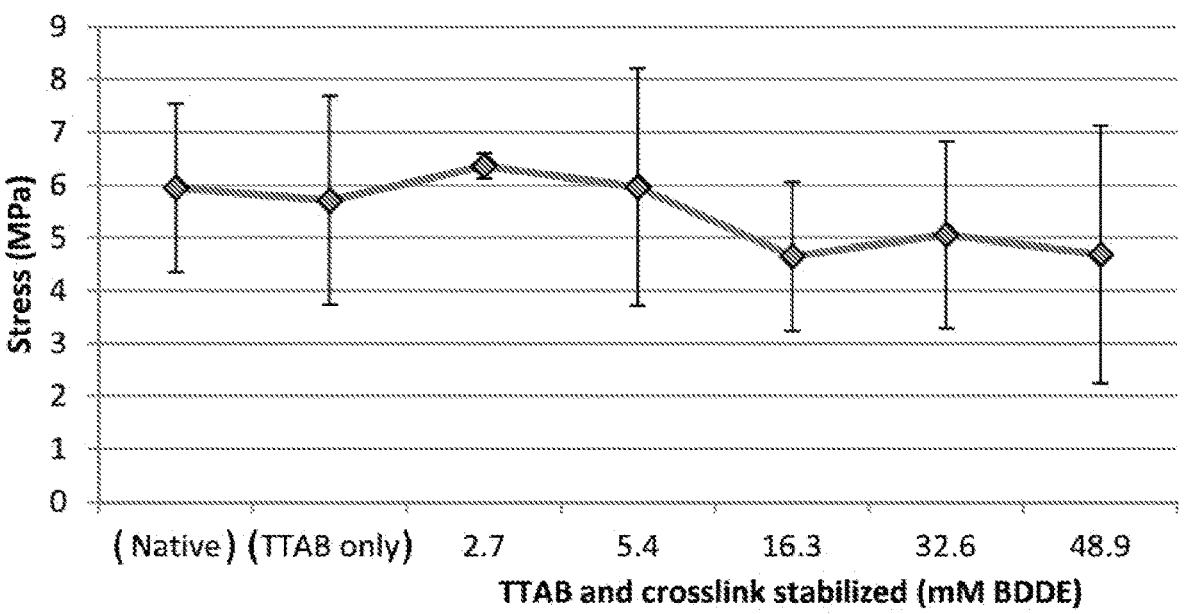
FIG. 8 illustrates an exemplary series of retention in compressive yield stress following cationic detergent treatment and crosslinking treatment according to an embodiment of the present invention.

Example 9: Retention of Biomechanical Strength in Processed Cartilage-Derived Implants As illustrated in FIG. 8, and corresponding Tables 5 and 6, cartilage-derived implants retain a comparable level of biomechanical strength (relative to the native, unprocessed, source cartilage). In summary, the compressive yield stress values of crosslinked cartilage following treatment with various concentrations of the crosslinker BDDE falls within the range of the natural variation of the compressive yield stress values for the source cartilage and cartilage treated with TTAB only, or within a statistically relevant deviation or error value for the range of the natural variation of the compressive yield strength value for the source cartilage and cartilage treated with TTAB only. Lower concentrations of BDDE tend to provide average compressive yield stress values closer to those of the untreated and TTAB only samples. Thus, without being bound to theory, fewer molecular bridges between molecular components of the cartilage-derived implant may result in a more naturally feeling and functioning implant sample.

Table 5 displays the average values of compressive yield strength for native source cartilage, cationic detergent treated cartilage-derived implants, and crosslink stabilized cartilage-derived implants. Table 6 displays the replicate data for each tested concentration from which the averages in Table 5 were derived.

TABLE 5

| | BDDE Conc. (mM) | Compressive Yield Stress [MPa] | Std. Dev. |
|---|---|---|---|
| Native | 0 | 5.9 | 1.6 |
| TTAB only | 0 | 5.7 | 2.0 |
| TTAB and | 2.7 | 6.4 | 0.2 |
| Crosslinked | 5.4 | 6.0 | 2.2 |
| | 16.3 | 4.7 | 1.4 |
| | 32.6 | 5.1 | 1.8 |
| | 48.9 | 4.7 | 2.4 |

TABLE 6

| Porcine Source ID | BDDE (mM) | Compressive Stress at Yield (Slope threshold 40%) [MPa] |
|---|---|---|
| Native | | |
| e1 | 0 | 8.46544 |
| e1 | 0 | 5.71183 |
| c1 | 0 | 5.92684 |

TABLE 6-continued

| Porcine Source ID | BDDE (mM) | Compressive Stress at Yield (Slope threshold 40%) [MPa] |
|---|---|---|
| c1 | 0 | 6.95109 |
| b1 | 0 | 7.574 |
| b1 | 0 | 7.40103 |
| a7 | 0 | 4.09508 |
| a7 | 0 | 6.98408 |
| b7 | 0 | 5.35001 |
| b7 | 0 | 8.70031 |
| e7 | 0 | 3.19387 |
| e7 | 0 | 2.70819 |
| c7 | 0 | 5.28639 |
| c7 | 0 | 8.75197 |
| d7 | 0 | 6.14027 |
| d7 | 0 | 5.06639 |
| f7 | 0 | 5.50741 |
| f7 | 0 | 5.1443 |
| a8 | 0 | 3.45803 |
| a8 | 0 | 6.83257 |
| b8 | 0 | 7.40979 |
| b8 | 0 | 5.4875 |
| c8 | 0 | 6.71761 |
| c8 | 0 | 5.79286 |
| d8 | 0 | 8.24821 |
| d8 | 0 | 5.63203 |
| e8 | 0 | 5.52638 |
| e8 | 0 | 5.65551 |
| f8 | 0 | 4.07177 |
| f8 | 0 | 4.63247 |
| | Average | 5.947441 |
| | Std Dev | 1.591823275 |
| TTAB only 2 mg/mL (6 mM) | e1 | 0 | 2.94327 |
| | e1 | 0 | 3.70036 |
| | b1 | 0 | 9.67307 |
| | a8 | 0 | 6.19974 |
| | a8 | 0 | 6.3228 |
| | e8 | 0 | 5.02933 |
| | e8 | 0 | 5.57308 |
| | c8 | 0 | 4.87214 |
| | c8 | 0 | 7.07648 |
| | Average | 5.71003 |
| | Std Dev | 1.970598781 |
| TTAB and Crosslinked | a7 | 2.7 | 6.36171 |
| | a7 | 2.7 | 6.15209 |
| | e7 | 2.7 | 6.39091 |
| | e7 | 2.7 | 6.70959 |
| | f7 | 2.7 | 6.50053 |
| | f7 | 2.7 | 6.05617 |
| | Average | 6.361833333 |
| | Std Dev | 0.235982742 |
| TTAB and Crosslinked | a7 | 5.4 | 4.09056 |
| | a7 | 5.4 | 4.9767 |
| | b7 | 5.4 | 8.73461 |
| | b7 | 5.4 | 8.86657 |
| | f7 | 5.4 | 4.04974 |
| | f7 | 5.4 | 5.061 |
| | Average | 5.963196667 |
| | Std Dev | 2.238996542 |
| TTAB and Crosslinked | d7 | 16.3 | 5.32683 |
| | d7 | 16.3 | 5.42817 |
| | b7 | 16.3 | 5.63404 |
| | b7 | 16.3 | 5.67955 |
| | f7 | 16.3 | 2.31331 |
| | f7 | 16.3 | 3.52935 |
| | Average | 4.651875 |
| | Std Dev | 1.400564944 |
| TTAB and Crosslinked | d7 | 32.6 | 3.62848 |
| | d7 | 32.6 | 5.13575 |
| | b7 | 32.6 | 4.44363 |
| | b7 | 32.6 | 3.0038 |
| | c7 | 32.6 | 7.6496 |
| | c7 | 32.6 | 6.5106 |
| | Average | 5.061976667 |
| | Std Dev | 1.75915338 |

TABLE 6-continued

| | Porcine Source ID | BDDE (mM) | Compressive Stress at Yield (Slope threshold 40%) [MPa] |
|---|---|---|---|
| TTAB and Crosslinked | d7 | 48.9 | 2.38656 |
| | d7 | 48.9 | 3.77973 |
| | e7 | 48.9 | 7.47065 |
| | e7 | 48.9 | 7.8696 |
| | c7 | 48.9 | 2.31853 |
| | c7 | 48.9 | 4.27466 |
| | | Average | 4.683288333 |
| | | Std Dev | 2.440180521 |

Example 10: Enzyme Digestion Assay 800 mg of each sample was rinsed 2×5 minutes in ultra-pure water. Samples were then cut in half and weights of each half were recorded. One half was incubated in 150 U/mL Type 1A collagenase in a 50 mM TES, 0.36 CaCl$_2$, pH 7.4 buffer for 72 hr at 37° C. followed by 3×5 minute rinses in ultrapure water. Both halves were freeze-dried and percent mass remaining was calculated as the ratio between the digested and non-digested samples dry mass/wet mass values.

Example 11: Enzymatic Resistance of Stabilized Cartilage-Derived Implants

Figure 9:
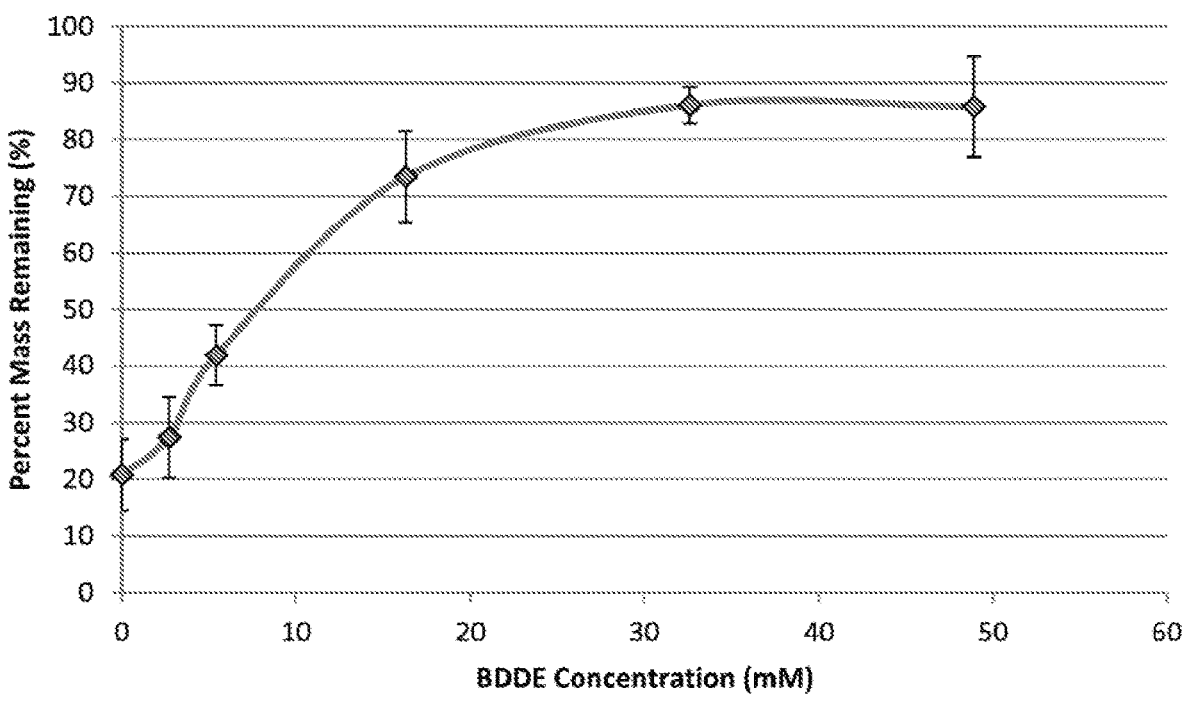
FIG. 9 illustrates an exemplary series of collagenase resistance following crosslinking treatment according to an embodiment of the present invention.

As illustrated in FIG. 9, and corresponding Tables 7 and 8, cartilage-derived implants can exhibit an increased resistance to enzymatic activity (e.g., enzymatic digestion). In summary, the percent cartilage mass remaining after exposure to collagenase, progressively increases substantially logarithmically within a relevant range of increasing concentrations of the crosslinker BDDE. Lower concentrations confer less resistance and higher concentrations generally confer greater resistance (e.g., to a maximum of greater than about 85-86% mass remaining) before leveling off. Accordingly, without being bound to theory, a greater number of molecular bridges between molecular components of the cartilage-derived implant may result in greater resistance against enzymatic activity.

Table 7 displays the average values of percent mass remaining for non-crosslinked cartilage-derived implants (TTAB only) and crosslink stabilized cartilage-derived implants following treatment with various concentrations of BDDE. Table 8 displays the replicate data for each tested concentration from which the averages in Table 7 were derived.

TABLE 7

| Group | BDDE (mM) | % Mass Remaining | Std Dev | Std Error |
|---|---|---|---|---|
| 1 | 0 | 20.79 | 6.28 | 4.44 |
| 2 | 2.7 | 27.40 | 7.12 | 5.03 |
| 3 | 5.4 | 41.91 | 5.29 | 3.74 |
| 4 | 16.3 | 73.44 | 8.02 | 5.67 |
| 5 | 32.6 | 86.04 | 3.21 | 2.27 |
| 6 | 48.9 | 85.78 | 8.87 | 6.27 |

TABLE 8

| | Collagenase treated | | | Control | | | | |
|---|---|---|---|---|---|---|---|---|
| Group | Wet weight (mg) | Dry weight (mg) | Dry/ Wet ratio | Wet weight (mg) | Dry weight (mg) | Dry/ Wet ratio | % Mass Remaining | % Mass Removed |
| 1 | 503.7 | 11.6 | 0.0230 | 542.1 | 88.2 | 0.1627 | 14.15 | 85.85 |
| 1 | 483.5 | 16.5 | 0.0341 | 605.4 | 95.7 | 0.1581 | 21.59 | 78.41 |
| 1 | 484.6 | 18 | 0.0371 | 499.7 | 69.7 | 0.1395 | 26.63 | 73.37 |
| 2 | 397.1 | 13.4 | 0.0337 | 401.8 | 50.3 | 0.1252 | 26.96 | 73.04 |
| 2 | 459.1 | 10.3 | 0.0224 | 370.4 | 40.5 | 0.1093 | 20.52 | 79.48 |
| 2 | 513.3 | 32.5 | 0.0633 | 428.4 | 78.1 | 0.1823 | 34.73 | 65.27 |
| 3 | 343.4 | 17.7 | 0.0515 | 370.6 | 43 | 0.1160 | 44.42 | 55.58 |
| 3 | 451.5 | 32.5 | 0.0720 | 396.7 | 79.7 | 0.2009 | 35.83 | 64.17 |
| 3 | 528.1 | 28.7 | 0.0543 | 464.3 | 55.5 | 0.1195 | 45.46 | 54.54 |
| 4 | 527.8 | 65.2 | 0.1235 | 366.7 | 69.4 | 0.1893 | 65.27 | 34.73 |
| 4 | 433.5 | 48.1 | 0.1110 | 405.9 | 55.4 | 0.1365 | 81.30 | 18.70 |
| 4 | 480.0 | 44.1 | 0.0919 | 412.6 | 51.4 | 0.1246 | 73.75 | 26.25 |
| 5 | 527.0 | 61.2 | 0.1161 | 533.4 | 75.2 | 0.1410 | 82.37 | 17.63 |
| 5 | 427.1 | 50.3 | 0.1178 | 329.9 | 44 | 0.1334 | 88.30 | 11.70 |
| 5 | 491.2 | 94.7 | 0.1928 | 572 | 126.1 | 0.2205 | 87.45 | 12.55 |
| 6 | 518.7 | 66.4 | 0.1280 | 580.4 | 80.7 | 0.1390 | 92.07 | 7.93 |
| 6 | 477.2 | 78 | 0.1635 | 589.5 | 127.4 | 0.2161 | 75.63 | 24.37 |
| 6 | 442.6 | 50.7 | 0.1146 | 504.7 | 64.5 | 0.1278 | 89.63 | 10.37 |

Example 12: Unit Conversions by Reagent

In some embodiments, certain reagents are provided at a concentration having a defined unit of measurement. One will appreciate that unit conversions as known in the art and/or as provided herein are also contemplate. For instance, Table 9, below, displays exemplary unit conversions for the cationic detergent TTAB, the zwitterionic detergent CHAPS, and the crosslinking agent BDDE.

TABLE 9

| Cationic Detergent: | | |
| --- | --- | --- |
| TTAB (mM) | TTAB (mg/mL) | TTAB (% w/v) |
| 23.8 | 8 | 0.8 |
| 11.9 | 4 | 0.4 |
| 5.9 | 2 | 0.2 |
| 3.0 | 1 | 0.1 |
| 1.5 | 0.5 | 0.05 |
| 0.7 | 0.25 | 0.025 |
| Zwitterionic Detergent: | | |
| CHAPS (mM) | CHAPS (mg/mL) | CHAPS (% w/v) |
| 8.1 | 5 | 0.5 |
| Crosslinking Agent: | | |
| BDDE (mM) | BDDE (% v/v) | BDDE (% w/v) |
| 0 | 0 | 0 |
| 2.7 | 0.05 | 0.055 |
| 5.4 | 0.1 | 0.11 |
| 16.3 | 0.3 | 0.33 |
| 32.6 | 0.6 | 0.66 |
| 48.9 | 0.9 | 1.0 |

While various aspects and embodiments have been disclosed herein, other aspects and embodiments are contemplated. The various aspects and embodiments disclosed herein are for purposes of illustration and are not intended to be limiting. It is noted that products, processes, compositions, kits, and methods according to certain embodiments of the present invention may include, incorporate, or otherwise comprise properties, features, components, members, and/or elements described in other embodiments described and/or disclosed herein. Thus, reference to a specific feature in relation to one embodiment should not be construed as being limited to applications only within said embodiment. In addition, various embodiments can be combined to form additional embodiments without departing from the scope of the invention or this disclosure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the products, processes, compositions, kits, and methods disclosed herein may be made without departing from the scope of the invention, which is defined in the appended claims. All changes which come within the meaning and range of equivalency of the claims are to be embraced within their scope. Various modifications that fall within the scope of the appended claims will be apparent to one skilled in the art.

What is claimed is:

1. A cartilage-derived tissue composition, comprising:
a cartilage-derived body comprising intact extra-cellular matrix and one or more molecular bridges between molecules of the extra-cellular matrix, the one or more molecular bridges selected from the group consisting of:
a molecular bridge formed between amine groups of one or more collagen fibrils;
a molecular bridge formed between hydroxyl groups of one or more glycosaminoglycan molecules;
a molecular bridge formed between a hydroxyl group of a glycosaminoglycan molecule and an amine group of a collagen fibril;
a sulfone-containing bridge; and
a bridge formed from treating the cartilage with a hydrocarbon diol reactive molecule having between 3 and 12 carbon atoms.

2. The composition of claim 1, wherein the one or more molecular bridges comprise butanediol.

3. The composition of claim 1, wherein the body includes a plurality of molecular bridges, including:
at least one molecular bridge between amine groups of one or more collagen fibrils;
at least one molecular bridge between hydroxyl groups of one or more glycosaminoglycan molecules; and/or
at least one a molecular bridge between a hydroxyl group of a glycosaminoglycan molecule and an amine group of a collagen fibril.

4. The composition of claim 1, wherein the body includes a plurality of molecular bridges including at least one hydrocarbon diol-containing bridge having between 3 and 12 carbon atoms and/or at least one sulfone-containing bridge.

5. The composition of claim 1, wherein the body includes a plurality of molecular bridges that occupy between 0.000001% and 20% of molecular groups selected from the group consisting of:
amine groups present in the body;
hydroxyl groups present in the body; and
amine and hydroxyl groups present in the body.

6. A cartilage-derived tissue composition, comprising:
an enzymatically resistant cartilage-derived body comprising intact extra-cellular matrix obtained by treating source cartilage with at least one multifunctional reactive molecule configured to form one or more molecular bridges between molecules of the source cartilage, the one or more molecular bridges selected from the group consisting of:
a molecular bridge formed between amine groups of one or more collagen fibrils;
a molecular bridge formed between hydroxyl groups of one or more glycosaminoglycan molecules;
a molecular bridge formed between a hydroxyl group of a glycosaminoglycan molecule and an amine group of a collagen fibril;
a sulfone-containing bridge; and
a bridge formed from treating the cartilage with a hydrocarbon diol reactive molecule having between 3 and 12 carbon atoms.

7. The composition of claim 6, wherein the at least one multifunctional reactive molecule is selected from the group consisting of a molecule comprising more than one and less than 5 reactive epoxide groups; divinyl sulfone; 1,4-butanediol diglycidyl ether (BDDE); 1,2,7,8-diepoxyoctane; and combinations thereof.

8. The composition of claim 6, wherein the one or more molecular bridges are not present in the source cartilage prior to treating the source cartilage with the at least one multifunctional reactive molecule.

9. The composition of claim 6, wherein the one or more molecular bridges comprise butanediol.

10. The composition of claim 6, wherein the body includes a plurality of molecular bridges, including:
at least one molecular bridge between amine groups of one or more collagen fibrils;
at least one molecular bridge between hydroxyl groups of one or more glycosaminoglycan molecules; and
at least one a molecular bridge between a hydroxyl group of a glycosaminoglycan molecule and an amine group of a collagen fibril.

11. The composition of claim 6, wherein the body includes a plurality of molecular bridges including at least one hydrocarbon diol-containing bridge having between 3 and 12 carbon atoms and/or at least one sulfone-containing bridge.

12. The composition of claim 6, wherein the body includes a plurality of molecular bridges that occupy between 0.000001% and 20% of molecular groups selected from the group consisting of:
amine groups present in the body;
hydroxyl groups present in the body; and
amine and hydroxyl groups present in the body.

13. The composition of claim 6, wherein the body is resistant to at least one of cellular infiltration and enzymatic digestion as compared to the source cartilage prior to treating the source cartilage with the at least one multifunctional reactive molecule.

14. The composition of claim 6, wherein the body has or exhibits one or more properties or characteristics selected from the group consisting of:
resistance against enzymatic digestion compared to the source cartilage;
biocompatibility for human implantation;
glycosaminoglycan content within 25% of the glycosaminoglycan content of the animal source cartilage;
type II collagen content within 25% of the type II collagen content of the animal source cartilage;
a mechanical property value substantially the same as a mechanical property value of the source cartilage;
a mechanical property value within 25% of a mechanical property value of the source cartilage; and
a mechanical property value within one standard deviation of an average mechanical property value of the source cartilage.

15. The composition of claim 14, wherein the mechanical property value is selected from the group consisting of a yield stress value, a yield strain value, a yield strain at break value, a compressive yield stress value, a compressive yield strain value, a compressive yield strain at break value, a Young's modulus value, a compressibility value, an elasticity value, an instantaneous stiffness value, a tensile strength value, a tensile strain value, a coefficient of friction value, a resilience value, and a shock absorption value.

16. The composition of claim 6, wherein the source cartilage is derived from an animal explant.

17. A cartilage-derived tissue composition, comprising:
a cartilage-derived body comprising intact extra-cellular matrix obtained by treating source cartilage with at least one multifunctional reactive molecule is selected from the group consisting of a molecule comprising more than one and less than 5 reactive epoxide groups; divinyl sulfone; 1,4-butanediol diglycidyl ether (BDDE); 1,2,7,8-diepoxyoctane; and combinations thereof.

18. The composition of claim 17, wherein the body comprises one or more molecular bridges between molecules of the extra-cellular matrix, the one or more molecular bridges selected from the group consisting of:
a bridge formed from treating the cartilage with a hydrocarbon diol reactive molecule having between 3 and 12 carbon atoms;
a sulfone-containing bridge;
a molecular bridge formed between amine groups of one or more collagen fibrils;
a molecular bridge formed between hydroxyl groups of one or more glycosaminoglycan molecules; and
a molecular bridge formed between a hydroxyl group of a glycosaminoglycan molecule and an amine group of a collagen fibril.

19. The composition of claim 17, wherein the one or more molecular bridges are not present in the source cartilage prior to treating the source cartilage with the at least one multifunctional reactive molecule.

20. The composition of claim 17, wherein the one or more molecular bridges comprise butanediol.

21. The composition of claim 17, wherein the body includes a plurality of molecular bridges, including:
at least one molecular bridge between amine groups of one or more collagen fibrils;
at least one molecular bridge between hydroxyl groups of one or more glycosaminoglycan molecules; and
at least one a molecular bridge between a hydroxyl group of a glycosaminoglycan molecule and an amine group of a collagen fibril.

22. The composition of claim 17, wherein the body includes a plurality of molecular bridges including at least one hydrocarbon diol-containing bridge having between 3 and 12 carbon atoms and/or at least one sulfone-containing bridge.

23. The composition of claim 17, wherein the body includes a plurality of molecular bridges that occupy between 0.000001% and 20% of molecular groups selected from the group consisting of:
amine groups present in the body;
hydroxyl groups present in the body; and
amine and hydroxyl groups present in the body.

24. The composition of claim 17, wherein the body is resistant to at least one of cellular infiltration and enzymatic digestion as compared to the source cartilage prior to treating the source cartilage with the at least one multifunctional reactive molecule.

25. The composition of claim 17, wherein the body has or exhibits one or more properties or characteristics selected from the group consisting of:
resistance against enzymatic digestion compared to the source cartilage;
biocompatibility for human implantation;
glycosaminoglycan content within 25% of the glycosaminoglycan content of the animal source cartilage;
type II collagen content within 25% of the type II collagen content of the animal source cartilage;
a mechanical property value substantially the same as a mechanical property value of the source cartilage;
a mechanical property value within 25% of a mechanical property value of the source cartilage; and a mechanical property value within one standard devia-
tion of an average mechanical property value of the
source cartilage.

26. The composition of claim 25, wherein the mechanical property value is selected from the group consisting of a yield stress value, a yield strain value, a yield strain at break value, a compressive yield stress value, a compressive yield strain value, a compressive yield strain at break value, a Young's modulus value, a compressibility value, an elasticity value, an instantaneous stiffness value, a tensile strength value, a tensile strain value, a coefficient of friction value, a resilience value, and a shock absorption value.

27. The composition of claim 17, wherein the source cartilage is derived from:

an intact extra-cellular matrix structure comprising glycosaminoglycans (GAGs) and/or (type II) collagen; and/or an animal explant, wherein the animal explant is optionally selected from the group consisting of septal cartilage, auricular cartilage, costal cartilage, and articular cartilage, and wherein the animal optionally selected from the group consisting of pig, horse, cow, canine, human, a non-human animal genetically deficient in expression of galactose-alpha-1,3-galactose, a non-human animal that has been genetically altered to express one or more human proteins, and a non-human animal that has been genetically altered to express one or more human proteins and that is genetically deficient in expression of galactose-alpha-1,3-galactose.

<div align="center">

\*    \*    \*    \*    \*

</div>